United States Patent
Chen et al.

(10) Patent No.: US 9,119,569 B2
(45) Date of Patent: Sep. 1, 2015

(54) METHOD AND APPARATUS FOR CALIBRATING A MOTION TRACKING SYSTEM

(71) Applicant: NANYANG TECHNOLOGICAL UNIVERSITY, Singapore (SG)

(72) Inventors: I-Ming Chen, Singapore (SG); Qilong Yuan, Singapore (SG)

(73) Assignee: Nanyang Technological University, Singapore (SG)

( * ) Notice: Subject to any disclaimer, the term of this patent is extended or adjusted under 35 U.S.C. 154(b) by 0 days.

(21) Appl. No.: 14/356,325

(22) PCT Filed: Nov. 7, 2012

(86) PCT No.: PCT/SG2012/000423
§ 371 (c)(1),
(2) Date: May 5, 2014

(87) PCT Pub. No.: WO2013/070171
PCT Pub. Date: May 16, 2013

(65) Prior Publication Data
US 2014/0303524 A1    Oct. 9, 2014

Related U.S. Application Data

(60) Provisional application No. 61/557,075, filed on Nov. 8, 2011.

(51) Int. Cl.
*A61B 5/103* (2006.01)
*A61B 5/117* (2006.01)
*A61B 5/11* (2006.01)
*A61B 5/00* (2006.01)

(52) U.S. Cl.
CPC ............. *A61B 5/1121* (2013.01); *A61B 5/11* (2013.01); *A61B 5/1126* (2013.01); *A61B 5/6801* (2013.01); *A61B 5/7225* (2013.01); *A61B 2560/0223* (2013.01)

(58) Field of Classification Search
CPC ...... A61B 5/11; A61B 5/1126; A61B 5/7225; A61B 5/1121; A61B 5/6801; A61B 2560/0223
USPC .......... 600/587, 595; 345/474; 73/865.4, 511; 702/94
See application file for complete search history.

(56) References Cited

U.S. PATENT DOCUMENTS

2008/0262772 A1* 10/2008 Luinge et al. ............. 702/94
2009/0322763 A1   12/2009 Bang et al.

FOREIGN PATENT DOCUMENTS

| EP | 1406215 A1 | 4/2004 |
| WO | 0237827 A2 | 5/2002 |
| WO | 2013070171 A1 | 5/2013 |

OTHER PUBLICATIONS

Foreign Communication From a Related Counterpart Application, International Search Report dated Jan. 25, 2013, International Application No. PCT/SG2012/000423 filed on Nov. 7, 2012.
Foreign Communication From a Related Counterpart Application, International Preliminary Report on Patentability dated Dec. 17, 2013, International Application No. PCT/SG2012/000423 filed on Nov. 7, 2012.

* cited by examiner

Primary Examiner — Rene Towa

(57) ABSTRACT

Methods and apparatus are provided for calibrating a motion tracking system (100) including a plurality of orientation sensors (102a-103h) attached to a plurality of body segments (104a-105h) of a user (9101). The methods and apparatus receive a first set of orientation signals from a first set of the orientation sensors (102a-102g). The first set of orientation signals associated with a first pair of the body segments (102a, 102f) matching a first set of predetermined positions. The skeleton dimension of the user and the mapping between the body segments and the corresponding attached sensors (102a-103h) are calibrated based on the first set of orientation signals. A first template including the first set of predetermined positions may be used, and the first pair of the body segments (104a, 104f) include the feet of the user. Receiving the first set of orientation signals includes receiving an orientation signal from each of the first set of sensors 102a-102g as the feet of the user (101) are placed on each of the first set of predetermined positions of the template.

22 Claims, 12 Drawing Sheets

METHOD AND APPARATUS FOR CALIBRATING A MOTION TRACKING SYSTEM

CROSS-REFERENCE TO RELATED APPLICATIONS

This application is a filing under 35 U.S.C. 371 as the National Stage of International Application No. PCT/SG2012/000423, filed Nov. 7, 2012, entitled "METHOD AND APPARATUS FOR CALIBRATING A MOTION TRACKING SYSTEM", which claims the benefit of and priority to U.S. Provisional Patent Application No. 61/557,075, filed Nov. 8, 2011, both of which are incorporated herein by reference in their entirety for all purposes.

TECHNICAL FIELD

The present invention relates to methods and apparatus for calibration and/or recalibration of motion tracking systems comprising a plurality of orientation sensors attached to a plurality of body segments of a user. In particular, the methods and apparatus are based on receiving a set of orientation signals from the sensors when a pair of body segments matches a set of predetermined positions, and calibrating the skeleton dimension of the user based on the set of orientation signals.

BACKGROUND

Tracking the motion of a human has been an important and open problem in many applications such as biomedical, special sports, clinical applications and entertainment. Among all the motion tracking technologies, integrated Inertial Measurement Unit (IMU) orientation sensors are currently used widely for spatial orientation tracking. Due to demand and advancements in manufacturing technology, IMU sensors have become smaller and cheaper with significant improvements in accuracy and reliability in human measurement. Over the next few years, IMU sensors may become the main orientation sensor used in motion tracking systems and related products for cinematic production, digital entertainment, high performance sports, and medical rehabilitation. For example, see J. Favre, B. Jolles, R. Aissaoui, and K. Aminian, "Ambulatory measurement of 3D knee joint angle," Journal of biomechanics, vol. 41, pp. 1029-1035, 2008; M. Brodie, A. Walmsley, and W. Page, "Fusion motion capture: a prototype system using inertial measurement units and GPS for the biomechanical analysis of ski racing," Sports Technology, vol. 1, pp. 17-28, 2008; Qilong Yuan, I-Ming Chen, and S. P. Lee, "SLAC: 3D Localization of Human Based on Kinetic Human Movement Capture," in Robotics and Automation (ICRA), 2011 IEEE International Conference on, Shanghai, China, 2011; C. Frigo, M. Rabuffetti, D. Kerrigan, L. Deming, and A. Pedotti, "Functionally oriented and clinically feasible quantitative gait analysis method," Medical and Biological Engineering and Computing, vol. 36, pp. 179-185, 1998; C. Goodvin, E. Park, K. Huang, and K. Sakaki, "Development of a real-time three-dimensional spinal motion measurement system for clinical practice," Medical and Biological Engineering and Computing, vol. 44, pp. 1061-1075, 2006; E. Bachmann, "Inertial and magnetic tracking of limb segment orientation for inserting humans into synthetic environments.," PhD Thesis, Naval Postgraduate School Monterey Calif., 2000.

However, to use IMU sensors to recover the motion of users from the sensor outputs or the orientation signals of the sensor, a calibration procedure is typically necessary to set the ground truth of the motion tracking system and subsequently optimise the performance of the motion tracking devices. Any motion tracking system or product of this nature requires a method and/or software for motion calibration.

Existing calibration methods depend on external measurement devices and regression analysis of the collected data. This means, these calibration procedures are very time consuming and processor intensive. In the calibration, the mappings from sensor orientations to the corresponding body segment orientations and the body segment dimensions are the parameters to be determined. For wearable motion tracking devices, after attaching all the sensors on the required body segments of a user, the mappings between the body segment orientation and the corresponding sensor orientation need to be calibrated to estimate the body movements of the user.

Even though the mapping calibration procedure for inertial motion capture (IMC) systems is less complicated than for optical, magnetic and ultrasonic based motion tracking systems, existing IMC systems still have many restrictions on the user (or subject), and are usually very heavily dependent on external devices.

For example, in the calibration procedures of Gypsy 190® IMC systems of MetaMotion® (e.g. see MetaMotion. (2010). http://www.metamotion.com) and MVN® systems of Xsens® (e.g. see X. Technologies. (2010). http://www.xsens.com and D. Roetenberg, H. Luinge, and P. Slycke, "Xsens MVN: full 6DOF human motion tracking using miniature inertial sensors," Xsens Technologies, 2009.), the users are required to face the magnetic north with a standing posture or "T" posture during the calibration. In this way, the body bearing orientation is known for calibration. However, the reference-north orientation is not always available, and a user cannot match the desired body bearing orientation exactly. More importantly, when the user conducts motion capture sessions for long durations, the sensors will move slightly on the body segments. In this case, recalibration of the system will be needed to continue precise motion capture. It is desirable to have a reliable and convenient procedure that can be conducted at anytime without and special requirements of the users (e.g. special range of motion or north orientations).

Besides the mapping, the skeleton dimensions are also very critical for precise motion representation. In many human postures or movements in surroundings, the skeleton model of the user needs to be precise enough to provide the exact posture or movements. For example, when the user holds their hands together, if the skeleton model is not accurate, in the captured posture, the two hands of the skeleton model may intersect with or separate from each other. When walking, if the estimated skeleton dimensions of the lower limb are smaller than the actual ones, the captured step length for walking is also shortened which leads to inaccurate body translation. When a user is sitting on a chair, the captured result may show they are not in contact with the chair if the skeleton model is estimated longer than the actual one. Before conducting human motion tracking, a skeleton calibration procedure is required to determine the skeleton dimension parameters for initialising motion tracking systems.

For precise motion tracking, measuring the body dimensions of the human has always been a challenging issue for all kinds of motion tracking systems (also known as Mocaps). Optical based motion tracking systems can estimate the body dimensions of the user by determining the center of rotation (COR) and axis of rotation (AOR) based on the statistic analysis of position of the markers attached on human body. However, these systems require a large number of markers and a large amount of data, which makes the estimation procedure very time consuming, complicated, and processor intensive (e.g. see M. Silaghi, R. Plankers, R. Boulic, P. Fua, and D. Thalmann, "Local and global skeleton fitting techniques for optical motion capture," Modelling and Motion Capture Techniques for Virtual Environments, pp. 26-40, 1998; or S. Gamage and J. Lasenby, "New least squares solutions for estimating the average centre of rotation and the axis of rotation," Journal of biomechanics, vol. 35, pp. 87-94, 2002). If the marker sets are not properly assigned, the result is usually inaccurate because of the skin movement effect and COR estimation algorithms. The estimated skeleton results also have asymmetric problems (skeleton dimension are not symmetric between the left and the right side). In addition, the high price of the optical motion capture systems makes them unattractive for the general public.

Some existing commercial inertial Mocaps systems determine the body skeleton dimensions based on external measurement devices. The Gypsy® system described above measures the skeleton model by taking a front and a side view of the user. The picture is then post-processed through a software called AutoCAL® to estimate the skeleton of the subject. Brodie et al built a 3-D anthropometry for skeleton dimensions measurement of subjects (e.g. see also M. A. D. Brodie, "Development of fusion motion capture for optimization of performance in alpine ski racing," PhD Thesis, Massey University, 2009). However, with more than ten parameters to adjust the system is complicated and time consuming for measuring the whole body skeleton dimensions. This cannot be performed by a single user, assistance is required. Post-processing the data to generate the skeleton model also takes time, and so is not suitable for real-time applications.

It is desirable to have a convenient, fast, and flexible calibration procedure that can reduce system set-up time of motion tracking systems. With quick calibration, users can run their motion tracking applications more efficiently anywhere and anytime. Therefore, there is a significant need to provide methods, apparatus and/or mechanisms for efficient and simple calibration/recalibration of motion tracking systems.

SUMMARY

It has been recognised here that whilst there are certain systems for calibrating and recalibrating motion tracking systems, none of these systems provide an efficient method, apparatus, and/or mechanism that allows accurate and rapid calibration and/or recalibration of a motion tracking system. The invention provides the advantage of being a convenient self-contained calibration method for use in initialising and/or for recalibrating sensor based motion tracking systems. Both the mappings and the skeleton dimensions of a user can be determined at the same time by a quick matching procedure based on a set of predetermined positions (e.g. a footprint/handprint matching procedure with pre-designed footprint/handprint template). Further advantages include not needing external assistant devices or special rules to constrain the users' movements, where the entire procedure can be completed by the user. This provides a fast, efficient and convenient way to get the motion tracking system prepared for applications in exercises, sports, entertainment, rehabilitation and other motion tracking based applications.

According to a first aspect of the invention there is provided a method of calibrating a motion tracking system including a plurality of orientation sensors attached to a plurality of body segments of a user. The method includes receiving a first set of orientation signals from a first set of the orientation sensors. The first set of orientation signals being associated with a first pair of the body segments matching a first set of predetermined positions. The method further includes calibrating the skeleton dimension of the user and the mapping between the body segments and the corresponding attached sensors based on the first set of orientation signals.

As an option, a first template includes the first set of predetermined positions and the first pair of the body segments includes the left and right feet of the user. The step of receiving the first set of orientation signals includes receiving an orientation signal from each of the first set of sensors as the left and right feet of the user are placed on each of the first set of predetermined positions of the template.

Optionally, the method includes receiving a second set of orientation signals from a second set of the sensors. The second set of orientation signals associated with a second pair of the body segments matching a second set of predetermined positions, where the second pair of body segments is different to the first pair of body segments. The step of calibrating further includes calibrating the skeleton dimension of the user and the mapping between the motion of the body segments and the corresponding attached second set of sensors based on the second set of orientation signals.

As an option, a second template includes the second set of predetermined positions and the second pair of the body segments includes the left and right hands of the user. The step of receiving the second set of orientation signals includes receiving an orientation signal from each of the second set of sensors as the left and right hands of the user are placed on each of the second set of predetermined positions of the second template.

As another option, the calibrating step further includes calculating a user bearing angle, t, based on the orientation signals from the first set of sensors when the first pair of body segments match an initial set of predetermined positions from the first set of predetermined positions. The mapping for each of the plurality of orientation sensors between the body segment and the corresponding sensor is calibrated based on the user bearing angle, $\Phi$. Optionally, calibrating the mapping includes determining, for each of the sensors, the mapping between said each sensor and the corresponding body segment motions. As an option, calculating the user bearing angle, t, is based on a standard skeleton model with the symmetric properties of the human body.

Optionally, the step of calibrating the mappings further includes calculating sensor orientation mapping matrices $R_{iM} = \text{rotz}(\Phi)^T R_{iS}$, for all of the sensors i, where $R_{iS}$ is an orientation matrix representing the measured orientation signal of sensor i with respect to a global coordinate frame at a particular measurement time, $R_{iM}$ is the sensor orientation mapping matrix of the sensor i in the corresponding body segment M, and $\text{rotz}(\Phi)$ is a rotation matrix representing a rotation of $\Phi$ radians about the z-axis and represents the estimated orientation of the body segment corresponding to the X-direction of the global coordinate frame. As an option, the method includes updating the motion of the body segments based on calculating $R_i = R_{iS} R_{iM}^T$, where $R_i$ is the orientation of the sensor i corresponding to the body segment frame M in the global coordinate frame.

As an option, calibrating the skeleton dimensions of the user further includes calculating from the first set of predetermined positions a corresponding set of step vectors between the first pair of body segments, and calculating lower body skeleton dimension parameters by solving a kinematic chain equation based on the step vectors and the corresponding orientation signals. The upper limb dimension is also calibrated in the same manner. The upper limb calibration uses handprint templates to calibrate.

Technically, the method for upper limb calibration is the same as lower limb calibration.

Optionally, the first set of body segments correspond to at least the set of vectors defined in the table of:

| Body Segment | Vector | From | To | Coordinate |
|---|---|---|---|---|
| Right Shank | $r_{R2}$ | Right | Right Ankle | $(a, b, c)^T$ |
| Right Thigh | $r_{R1}$ | Right Hip | Right Knee | $(d, e, f)^T$ |
| Pelvis | $r_0$ | Left Hip | Right Hip | $(0, g, 0)^T$ |
| Left Shank | $r_{L2}$ | Left Knee | Left Ankle | $(d, -e, f)^T$ |
| Left Thigh | $r_{L1}$ | Left Hip | Left Knee | $(a, -b, c)^T$ |

The kinematic chain equation for the lower body skeleton dimension for the first set of predetermined positions is based on:

$$\begin{bmatrix} r_s^1 \\ r_s^2 \\ \ldots \\ r_s^{n-1} \\ r_s^n \end{bmatrix} = \begin{bmatrix} A_{ftp}^1 \\ A_{ftp}^2 \\ \ldots \\ A_{ftp}^{n-1} \\ A_{ftp}^n \end{bmatrix} \cdot [a, b, c, d, e, f, g]^T,$$

where $r_s^m$ is the step vector for the m-th predetermined position for $1 \leq m \leq n$ of the first set of predetermined positions, and $A_{ftp}^m$ is the $A_{ftp}$ matrix associated with the m-th predetermined position, where $A_{ftp}$ defines a mapping between the lower body skeleton dimension parameters $[a, b, c, d, e, f, g]$ and the associated step vector and is defined by:

$$A_{ftp} = [R_{R2}+R_{L2} \cdot diag(-1,1,-1), R_{R1}+R_{L1} \cdot diag(-1,1,-1), R_0(:,2)]$$

where $R_X(:,i)$ is the i-th column of the matrix $R_X$, $diag(-1,1,-1)$ is a diagonal matrix, $R_{R2}$, $R_{L2}$, $R_{R1}$, $R_{L1}$, and $R_0$ are the orientations of the corresponding body segments calculated from the corresponding orientation signals and the corresponding calibrated mapping. As an option, the method includes weighting each of the step vectors with an adjustable set of weights depending on the importance of each step vector.

As another option, calibrating the skeletal dimensions of the user further includes calculating from the second set of predetermined positions a corresponding set of span vectors between the second pair of body segments, and calculating upper body skeleton dimension parameters by solving a kinematic chain equation based on the span vectors and the corresponding orientation signals.

Optionally, the second set of body segments correspond to at least the set of vectors defined in the table of:

| Body Segment | Vector | From | To | Coordinate |
|---|---|---|---|---|
| Right Upper Arm | $r_{R4}$ | Right Shoulder | Right Elbow | $(a_U, b_U, c_U)^T$ |
| Right Forearm | $r_{R5}$ | Right Elbow | Right Wrist | $(d_U, e_U, f_U)^T$ |
| D_Shoulders | $r_1$ | Left Shoulder | Right Shoulder | $(0, g_U, 0)^T$ |
| Left Upper Arm | $r_{L4}$ | Left Shoulder | Left Elbow | $(d_U, -e_U, f_U)^T$ |
| Left Forearm | $r_{L5}$ | Left Elbow | Left Wrist | $(a_U, -b_U, c_U)^T$ |

The kinematic chain equation for the upper body skeleton dimension for the second set of predetermined positions is based on:

$$\begin{bmatrix} r_{sU}^1 \\ r_{sU}^2 \\ \ldots \\ r_{sU}^{n-1} \\ r_{sU}^n \end{bmatrix} = \begin{bmatrix} A_{ftpU}^1 \\ A_{ftpU}^2 \\ \ldots \\ A_{ftpU}^{n-1} \\ A_{ftpU}^n \end{bmatrix} \cdot [a_U, b_U, c_U, d_U, e_U, f_U, g_U]^T,$$

where $r_{sU}^m$ is the span vector for the m-th predetermined position for $1 \leq m \leq n$ of the second set of predetermined positions, and $A_{ftpU}^m$ is the $A_{ftpU}$ matrix associated with the m-th predetermined position of the second set of predetermined positions, where $A_{ftpU}$ defines a mapping between the upper body skeleton dimension parameters $[a_U, b_U, c_U, d_U, e_U, f_U, g_U]$ and the associated span vector and is defined by: $A_{ftpU} = [R_{R4}+R_{L4} \cdot diag(-1,1,-1), R_{R5}+R_{L5} \cdot diag(-1,1,-1), R_1(:,2)]$, where $R_X(:,i)$ is the i-th column of the matrix $R_X$, $diag(-1,1,-1)$ is a diagonal matrix, $R_{R4}$, $R_{L4}$, $R_{R5}$, $R_{L5}$, and $R_1$, are the orientations of the corresponding body segments calculated from the corresponding orientation signals and the corresponding calibrated mapping. As an option, the method includes weighting each of the span vectors with an adjustable set of weights depending on the importance of each span vector.

Optionally, the method further includes a step of recalibrating the motion tracking system by recalculating a user bearing angle, $\Phi$, based on the orientation signals from the first set of sensors when the first pair of body segments match an initial set of predetermined positions from the first set of predetermined positions, and calibrating the mapping for each of the plurality of orientation sensors between the body segment and the corresponding sensor based on the user bearing angle, $\Phi$.

According to a second aspect of the invention there is provided a method for recalibrating a motion tracking system including a plurality of orientation sensors attached to a plurality of body segments of a user. The method includes receiving a first set of orientation signals from a first set of the orientation sensors, the first set of orientation signals associated with a first pair of the body segments matching a set of predetermined positions. A new user bearing angle, $\Phi$, is calculated based on the orientation signals from the first set of sensors The mapping for each of the plurality of orientation sensors between the body segment and the corresponding sensor is calibrated based on the user bearing angle, $\Phi$.

As an option, the methods include storing the calibrated skeleton dimensions and the mapping for use in tracking the motion of the user. Optionally, the orientation sensors are at least one of the sensors from the group of: orientation tracking devices, magnetic trackers, inertial measurement units, marker groups, or other sensing devices that provide spatial orientation. As an option, the mapping calibration and the skeleton dimension calibration are completed during the same template matching procedure.

According to a third aspect of the invention there is provided an apparatus for calibrating a motion tracking system including a plurality of sensors attached to a plurality of body segments of a user. The apparatus includes a receiver, a processor and a memory, the processor being connected to the receiver and the memory. The receiver is adapted to receive a first set of orientation signals from a first set of the orientation sensors, where the first set of orientation signals are associated with a first pair of the body segments matching a first set of predetermined positions. The processor is adapted to calibrate the skeleton dimension of the user and the mapping between the body segments and the corresponding attached sensors based on the first set of orientation signals.

Optionally, a first template includes the first set of predetermined positions and the first pair of the body segments includes the left and right feet of the user. The receiver is further adapted to receive an orientation signal from each of the first set of sensors as the left and right feet of the user are placed on each of the first set of predetermined positions of the template.

As an option, the receiver is further adapted to receive a second set of orientation signals from a second set of the sensors, the second set of orientation signals associated with a second pair of the body segments matching a second set of predetermined positions, wherein the second pair of body segments are different to the first pair of body segments. The processor is further adapted to calibrate the skeleton dimensions of the user and the mapping between the motion of the body segments and the corresponding attached second set of sensors based on the second set of orientation signals.

As another option, a second template comprises the second set of predetermined positions and the second pair of the body segments includes the left and right hands of the user. The receiver is further adapted to receive an orientation signal from each of the second set of sensors as the left and right hands of the user are placed on each of the second set of predetermined positions of the second template.

Optionally, the processor is further adapted to calculate a user bearing angle, t, based on the orientation signals from the first set of sensors when the first pair of body segments match an initial set of predetermined positions from the first set of predetermined positions. The processor is further adapted to calibrate the mapping for each of the plurality of orientation sensors between the body segment and the corresponding sensor based on the user bearing angle, $\Phi$.

As an option, the processor is further adapted to calibrate the mappings by calculating sensor orientation mapping matrices $R_{iM} = \text{rotz}(\Phi)^T R_{iS}$, for all of the sensors i, where $R_{iS}$ is an orientation matrix representing the measured orientation signal of sensor i with respect to a global coordinate frame at a particular measurement time, $R_{iM}$ is the sensor orientation mapping matrix of the sensor i in the corresponding body segment M, and $\text{rotz}(\Phi)$ is a rotation matrix representing a rotation of $\Phi$ radians about the z-axis and represents the estimated orientation of the body segment corresponding to the initial set of predetermined positions. Optionally, the processor is further adapted to update the motion of the body segments based on calculating $R_i = R_{iS} R_{iM}^T$, where $R_i$ is the orientation of the sensor i corresponding to the body segment M in the global coordinate frame.

As another option, the processor is further adapted to calibrate the skeleton dimensions of the user by calculating from the first set of predetermined positions a corresponding set of step vectors between the first pair of body segments, and calculating lower body skeleton dimension parameters by solving a kinematic chain equation based on the step vectors and the corresponding orientation signals.

Optionally, the processor is further adapted to calibrate the skeletal dimensions of the user by calculating from the second set of predetermined positions a corresponding set of span vectors between the second pair of body segments, and calculating upper body skeleton dimension parameters by solving a kinematic chain equation based on the span vectors and the corresponding orientation signals.

As an option, the processor is further adapted to recalibrate the motion tracking system by recalculating a new user bearing angle, t, based on the orientation signals from the first set of sensors when the first pair of body segments match an initial set of predetermined positions from the first set of predetermined positions. The processor is also adapted to calibrate the mapping for each of the plurality of orientation sensors between the body segment and the corresponding sensor based on the user bearing angle, $\Phi$.

According to a fourth aspect of the invention there is provided an apparatus for recalibrating a motion tracking system including a plurality of orientation sensors attached to a plurality of body segments of a user. The apparatus comprising a receiver, a processor and a memory, the processor connected to the receiver and the memory. The receiver is adapted to receive a first set of orientation signals from a first set of the orientation sensors, the first set of orientation signals associated with a first pair of the body segments matching a set of predetermined positions. The processor is adapted to calculate a user bearing angle, $\Phi$, based on the orientation signals from the first set of sensors. The processor is also adapted to calibrate the mapping for each of the plurality of orientation sensors between the body segment and the corresponding sensor based on the user bearing angle, $\Phi$.

As an option in the above apparatuses, the memory is adapted to store the calibrated skeleton dimensions and/or the mapping for use in tracking the motion of the user. The orientation sensors are at least one of the sensors from the group of: orientation tracking devices, magnetic trackers, inertial measurement units, marker groups, or other sensing devices that provide spatial orientation.

According to a fifth aspect of the invention, there is provided a computer program, comprising computer readable code which, when executed on a processor or apparatus as described, causes the processor or apparatus to perform the methods and operations described. The invention also provides a computer program product comprising a computer readable medium and a computer program as described, where the computer program is stored on the computer readable medium.

The invention provides the further advantages of not being dependent on external devices or requiring reference directions that are pre-defined to restrict the user. According to the present invention, in any environment, the user only needs to conduct the calibration procedure following the set of pre-defined positions (or the template) before using the motion tracking system. This allows use of the method in exercises and sports training within flexible environments where the north orientation is not necessarily known, and in medical care which takes place in hospital or home environments.

The invention provides the advantage of a convenient and efficient calibration procedure that can be completed within a few minutes (e.g. two minutes) to determine all the parameters needed for motion tracking. Since no extra adjustment or post-processing of the data is required, the applications can be conducted immediately after this procedure has completed. This is particularly useful for applications like exercise and entertainment, where users want to conduct the exercise or game as soon as possible. The recalibration procedure only takes around 20 seconds to correct the effects from the shift of all sensors. It can show great advantage in applications with long duration and dynamic behaviors.

The present invention provides the further advantage that the methods for calibration and recalibration are applicable to all wearable orientation sensors or measurement devices such as, but not limited to, for example, IMUs, magnetic trackers and optical marker-based systems.

BRIEF DESCRIPTION OF THE DRAWINGS

In order that the invention may be more fully understood, some of the embodiments of the invention will now be described, by way of example only, with reference to the accompanying drawings, in which.

DETAILED DESCRIPTION

Figure 1:
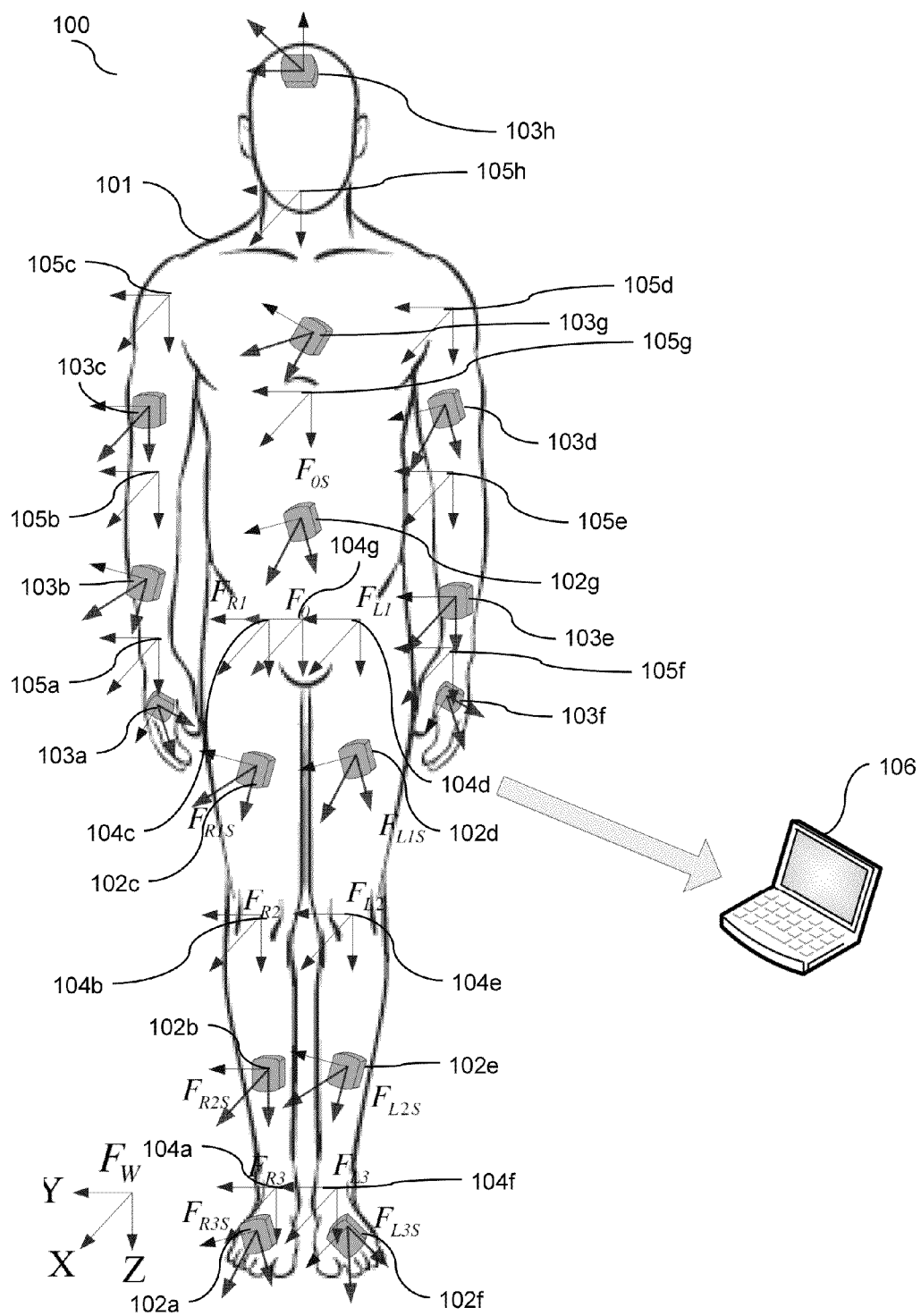
FIG. 1 illustrates an example of an orientation based motion tracking (or capture) system including a data processing computer.

In order to overcome the problems identified above with calibration/recalibration of motion tracking systems, methods and apparatus are described for use in efficiently calibrating and/or recalibrating motion tracking systems comprising a plurality of orientation sensors attached to a plurality of body segments of a user. The invention relates to an efficient "template-based" method for calibration of orientation measurement sensor based motion tracking systems. The calibration method optimizes the 3D dimension of the acting user body segments (subject limbs) and the coordinated mapping between the sensor motion and the body segment motion. The orientation sensor (e.g. an IMU) measures the data that can be processed to precise orientation measurement. Based on the orientation measurement of the body segments and a predetermined set of positions (e.g. a known footprint (handprint) distance on a template), an efficient calibration algorithm for use on an apparatus, such as for example a microcontroller, integrated circuit, or a computer such as a personal computer (PC), may be used to determine all the kinematic parameters before conducting the motion capture for various applications.

Various examples of the invention may include self-contained calibration methods for initialising and/or re-calibrating an orientation sensor-based motion tracking systems. The coordinate mappings (e.g. sensor frames to body segment frames) and the human skeleton dimensions can be determined simultaneously using sets of predetermined positions for corresponding sets of body segments and used for calibrating the skeleton dimensions.

By way of example only, the sets of predetermined positions may be located as footprint patterns or handprint patterns on a pre-printed foot template for lower limb/body segment calibration and a hand template for upper limb/body segment calibration, respectively. The user steps on the footprint patterns (or places their hands on the handprint patterns) with a number of different foot (and hand) print pairs. From this, the 3D skeletal dimensions (based on a human kinematic model) and the coordinate mappings can be determined automatically. The same algorithm may be used for both upper and lower body segments. In long duration motion tracking, the sensors can shift on the attached body segments and a quick and self-dependent recalibration procedure may be used to eliminate the shifting effect.

The calibration and recalibration methods and apparatus according to the invention have little restrictions and require neither external assistant devices, such as cameras, ultrasonic sensors, or rulers for setting the external references. The methods and apparatus according to the invention may be used for both indoor and outdoor environments without any modification. In addition, the entire calibration procedure can be completed by the user alone without additional help in a short time frame, e.g. typically within five minutes. The calibration and recalibration methods and apparatus according to the invention provide a fast and convenient way for preparing a motion tracking system for applications in exercises, sports, entertainments.

FIG. 1 illustrates an example of an orientation based motion tracking (or capture) system 100 including a user 101, the motion tracking system 100 including a plurality of orientation sensors 102a-102g and 103a-103h that are wearable or attached to said user 101 on corresponding plurality of body segments 104a-104g and 105a-105h, respectively. The plurality of orientation sensors 102a-102g and 103a-103h send orientation signals to a computer 106 for analysis such as calibration and/or recalibration of the motion tracking system 100. The plurality of sensors 102a-102g and 103a-103h may include a first set of orientation sensors 102a-102g and a second set of orientation sensors 103a-103g. It is to be appreciated that the first and second sets of sensors 102a-102g and 103a-103g may overlap and include one or more sensors from the other set of sensors. For example, although the orientation sensors 102g and 103g are placed on the torso body segments 104g and 105g, respectively, user 101 may instead use only one sensor for the torso body segments 104g and 105g such that this sensor is included in both the first and second sets of sensors. The computer 106 may perform a method for calibrating the motion tracking system 100 according to the invention.

Figure 2A:
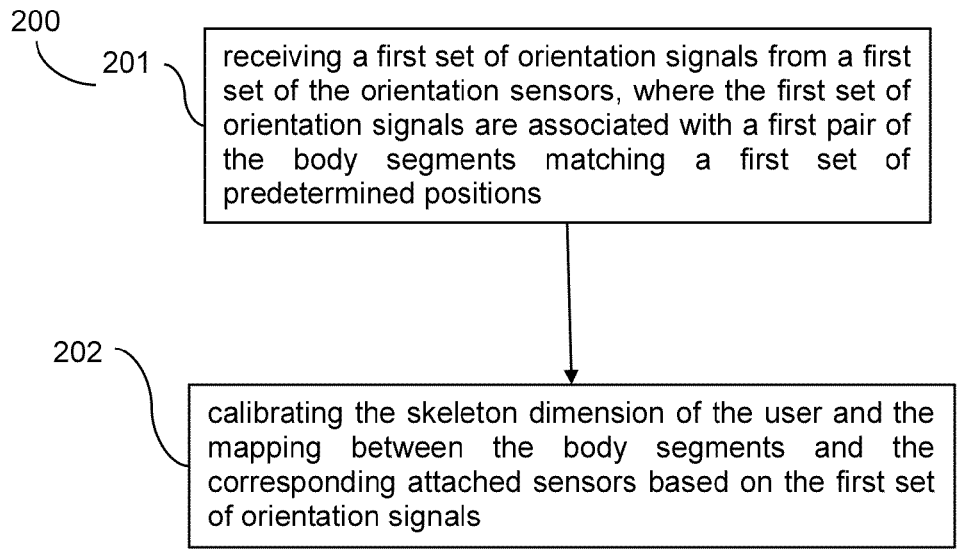
FIG. 2a illustrates an example method according to the invention for calibrating a first set of sensors of a motion tracking system.

FIG. 2a illustrates an example method 200 of calibrating a motion tracking system 100 according to the invention. As described in FIG. 1, the motion tracking system 100 includes a plurality of orientation sensors 102a-103h attached to a plurality of body segments 104a-105h of a user 101. The method 200 includes the following steps:

201. Receiving a first set of orientation signals from a first set of the orientation sensors 102a-102g. The first set of orientation signals being associated with a first pair of the body segments 104a and 104f matching a first set of predetermined positions.

202. Calibrating the skeleton dimension of the user 101 and the mapping between the body segments 104a-105h and the corresponding attached sensors 102a-103h based on the first set of orientation signals.

As an option, a first template includes the first set of predetermined positions and the first pair of the body segments includes the left and right feet of the user. The step of receiving 201 the first set of orientation signals includes receiving an orientation signal from each of the first set of sensors 102a-102g as the left and right feet 104f and 104a of the user 101 are placed on each of the first set of predetermined positions of the template.

Figure 2B:
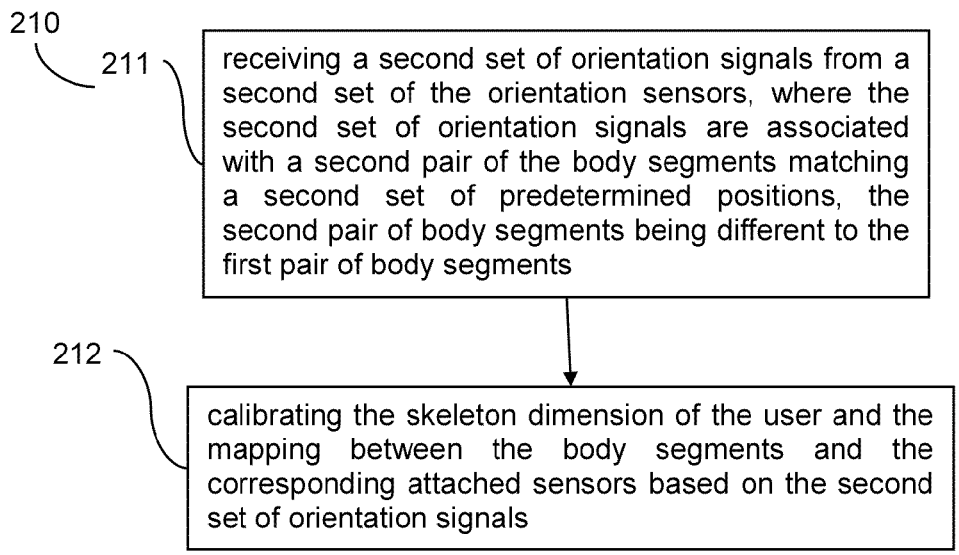
FIG. 2b illustrates an example method according to the invention for calibrating a second set of sensors of a motion tracking system.

FIG. 2b illustrates another example method 210 of calibrating a motion tracking system 100 according to the invention. The method includes the following steps:

211. Receiving a second set of orientation signals from a second set of the sensors 103a-103h. The second set of orientation signals associated with a second pair of the body segments 105a and 105f matching a second set of predetermined positions, where the second pair of body segments 105a and 105f are different to the first pair of body segments 104a and 104f.

212. Calibrating the skeleton dimension of the user 101 and the mapping between the motion of the body segments 105a-105h and the corresponding attached sensors 102a-105h based on the second set of orientation signals.

As an option, a second template includes the second set of predetermined positions and the second pair of the body segments 105a and 105f include the left and right hands of the user 101. The step of receiving 211 the second set of orientation signals includes receiving an orientation signal from each of the second set of sensors 103a-103g as the left and right hands of the user 101 are placed on each of the second set of predetermined positions of the second template.

Both methods 200 and 210 may be implemented together such that a whole skeleton model may be generated based on the calibrated skeleton dimensions. As another option, the calibrating steps 202 and/or 212 further includes calculating a user bearing angle, t, based on the orientation signals from the first set of sensors 102a-102g when the first pair of body segments 104a and 104f match an initial set of predetermined positions from the first set of predetermined positions. The mapping for each of the plurality of orientation sensors 102a-103h between the body segments 104a-105h and the corresponding sensors 102a-103h is calibrated based on the user bearing angle, Φ.

The step of calibrating the skeleton dimensions of the user 202 may further include calculating from the first set of predetermined positions a corresponding set of step vectors between the first pair of body segments 104a and 104f, and calculating lower body skeleton dimension parameters by solving a kinematic chain equation based on the step vectors and the corresponding orientation signals. The step of calibrating the skeletal dimensions of the user 212 may further include calculating from the second set of predetermined positions a corresponding set of span vectors between the second pair of body segments 105a and 105f, and calculating upper body skeleton dimension parameters by solving another kinematic chain equation based on the span vectors and the corresponding orientation signals.

It is to be appreciated that both methods 200 and 210 may be implemented separately or together. The following description provides further examples of the methods and apparatus according to the invention and further elaborates on the calibration based on matching the first and/or second pair of body segments 104a/104f and 105a/105f, respectively, onto a first and second set of predetermined positions, respectively.

FIGS. 3-9 illustrates other examples of methods of calibrating/recalibrating a motion tracking system according to the invention. These methods are template-based methods, which can be used for calibrating the 3D skeleton model and the coordinate mappings between a body frame (or body segments 104a-104g and 105a-105h) and a sensor frame (or the plurality of sensors 102a-102g and 103g-103h). For simplicity, the reference numerals of FIG. 1 will be used for similar or the same components and elements.

Referring to FIG. 1, the wearable orientation sensors (or measurement units) 102a-103h, which sense their own spatial orientations, are attached on the body segments 104a-105h (limbs) of the user. The computer 106 is used to collect the sensor outputs. The calibration procedures are conducted following the first set of predetermined positions as a footprint template and the second set of predetermined positions as a handprint template. A computer program based on an efficient algorithm for implementing the methods according to the invention operates in the computer 106 to determine the 3D skeleton model and the coordinate mappings which translate the sensor motion to the actual user motion.

Figure 3:
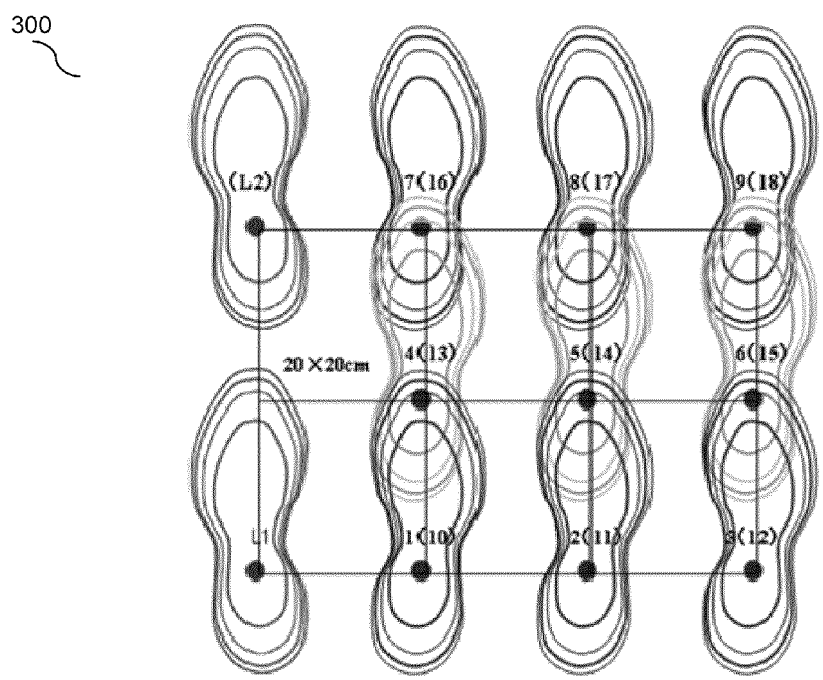
FIG. 3 illustrates an example footprint template for lower body segment (limb) dimension calibration according to the invention.

For the template method for calibrating the lower body segments a footprint template is used. An example footprint template 300 is illustrated in FIG. 3. In this example, the footprint template 300 is illustrated, by way of example, as having 11 footprints (two for the left foot and nine for the right foot), which define the first set of predetermined positions. Although the footprint template 300 has two footprint positions for the left foot and nine footprint positions for the right foot, it is to be appreciated by the person skilled in the art that a mirror image footprint template is also possible having two footprints for the right foot and nine footprints for the left foot. For simplicity, and by way of example only, the template methods will be described with reference to footprint template 300.

The footprints are arranged within a flat area. By way of example only, the distance between adjacent footprints is 20 cm along both the-X and the Y-direction. Although the footprint template 300 is described having a distance of 20 cm between adjacent footprints, it is to be appreciated by a person skilled in the art that other distances may be used depending on the size and type of the user 101.

In this example, the footprint template 300 has two positions available for the left foot and nine positions available for the right foot. This means there are a total of 2×9=18 choices for the user 101 to choose depending on different body sizes. For each footprint, there are many sizes available for persons with different foot sizes. When both feet are located at the desired footprints, the vector from the left foot to the right foot is known as the step vector and is calculated from the left footprint center to the right footprint center. Here the "center" point of each foot is an estimation of the projection of ankle joints when the footprint is matched. Therefore, the step vector also presents the relative position between two ankles. The example footprint template 300 may be suitable for users 101 from 145 cm to 200 cm+, which covers the majority of the adult population. For larger or smaller adults and children, it may be necessary to resize and print their specific footprint template.

Although the footprint template 300 is illustrated as having 11 footprints, it is to be appreciated by the person skilled in the art that the invention is not limited to the illustrated footprint template 300, but is applicable to any other suitable footprint template that may have a lower, equal, or higher number of footprints that are positioned in any suitable arrangement.

Figure 4:
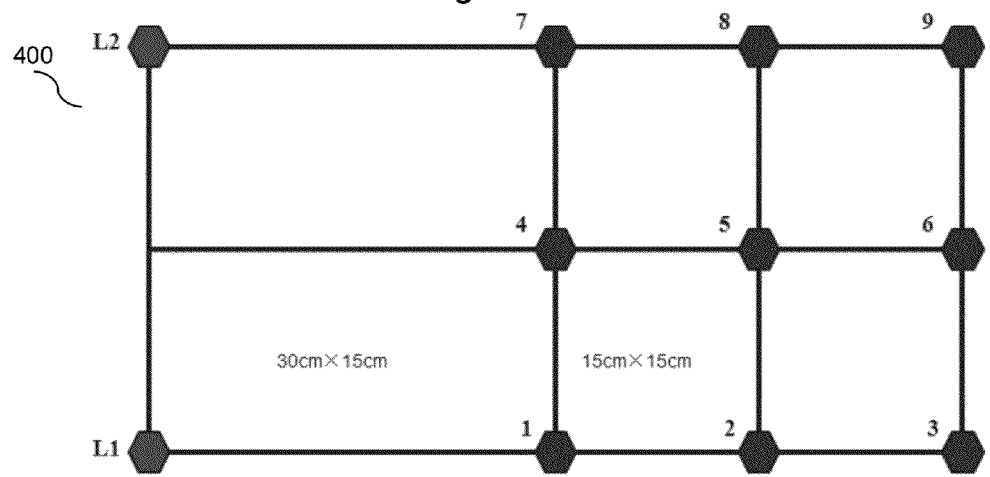
FIG. 4 illustrates an example template for calibration according to the invention of upper body segment dimensions (e.g. arms)

For the template method for calibrating the upper body segments a handprint template is used. An example handprint template 400 is illustrated, by way of example only, in FIG. 4. As for the footprint template 300, FIG. 4 illustrates the handprint template 400 as having 11 handprints (two for the left hand and nine for the right hand), which define a second set of predetermined positions. Although the handprint template 400 has two handprint positions for the left hand and nine handprint positions for the right hand, it is to be appreciated by the person skilled in the art that a mirror image handprint template is also possible having two handprints for the right hand and nine handprints for the left hand. For simplicity, and by way of example only, the template methods will be described with reference to handprint template 400.

The handprints are arranged within a flat area. By way of example only, the distance between adjacent handprints along both the-X and the Y-direction are shown in FIG. 4 as 30 cm and 15 cm, respectively. Although the handprint template 400 is described having a distance in the X-direction of 30 cm and a distance in the Y-direction of 15 cm between adjacent handprints, it is to be appreciated by a person skilled in the art that any other suitable distances may be used depending on the size and type of the user 101.

In this example, the handprint template 400 has two positions available for the left hand and nine positions for the right hand. Therefore, there are also 18 choices for the user to choose from depending on different body sizes. When both hands are located at the desired handprints, the vector from the left hand to the right hand is known as the span vector and is calculated from the left handprint center to the right handprint center. The "center" point of each hand is an estimation of the projection of wrist joints when the handprint is matched. The span vector also presents the relative position between two wrists. For larger or smaller adults and children, it may be necessary to resize and print their specific handprint template.

Although the handprint template 400 is illustrated as having 11 handprints, it is to be appreciated by the person skilled in the art that the invention is not limited to the illustrated handprint template 400, but is applicable to any other suitable handprint template that may have a lower, equal, or higher number of handprints that are positioned in any suitable arrangement.

Figure 5A:
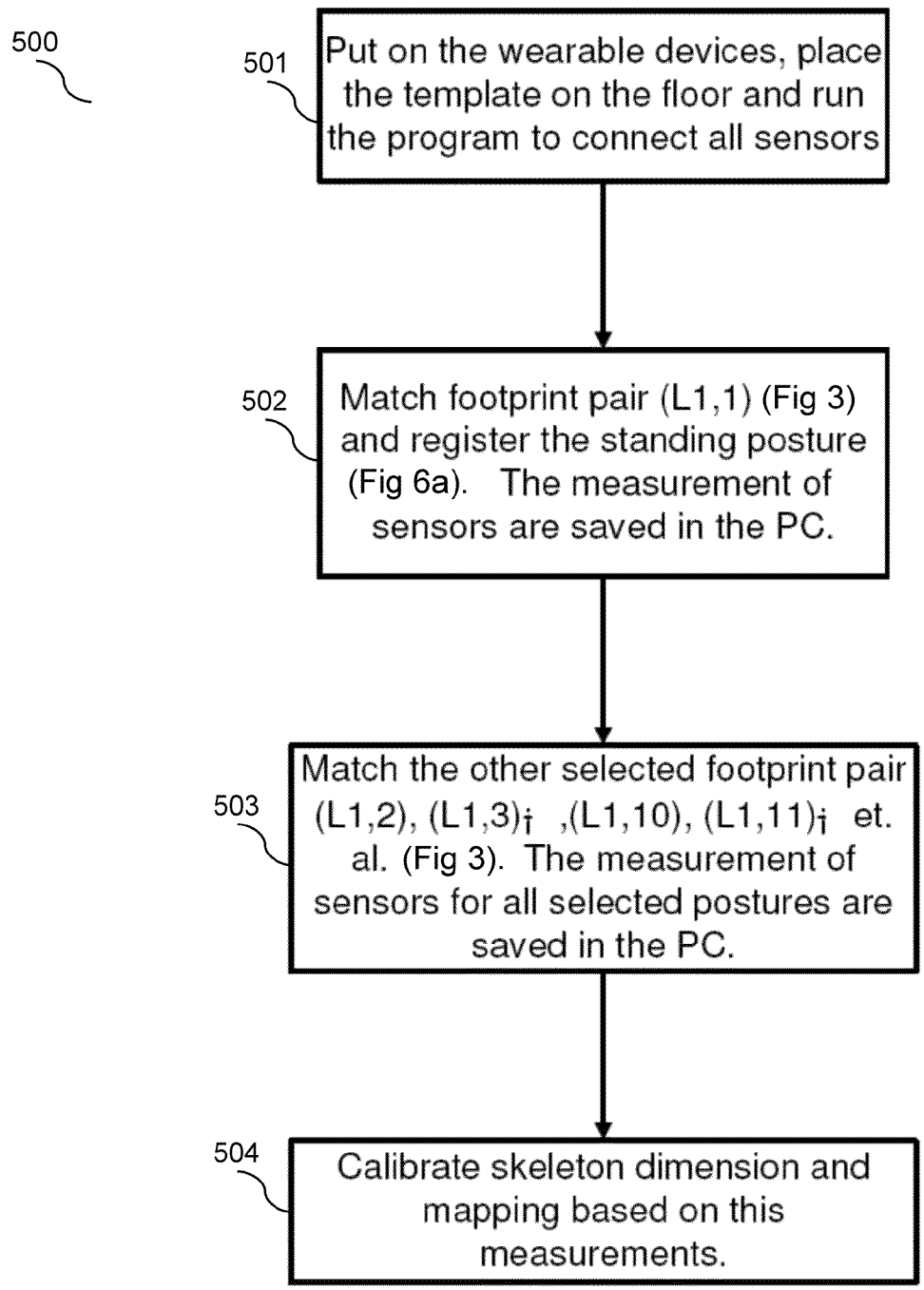
FIG. 5a illustrates another example method according to the invention for calibrating the dimensions for lower body segments in a motion tracking system.

FIG. 5a is a flow diagram illustrating a template based calibration procedure 500 for the lower body segments 104a-104g. The whole procedure may only require several footprint matching steps to be completed over a short period of time such as, for example, within two to five minutes. It is to be appreciated that the following steps include actions performed by the user 101, which in no way limit the calibration procedure performed by computer 106. The steps of the calibration procedure 500 are as follows:

501. The user wears the orientation sensors 102a-103h (e.g. IMU sensors), and runs the computer program to connect these sensors 102a-103h to the computer 106. Once completed, the computer 106 may now receive orientation signals from the sensors 102a-103h; the orientation signals include data representative of the orientations of the sensors 102a-103h.

Figure 6A:
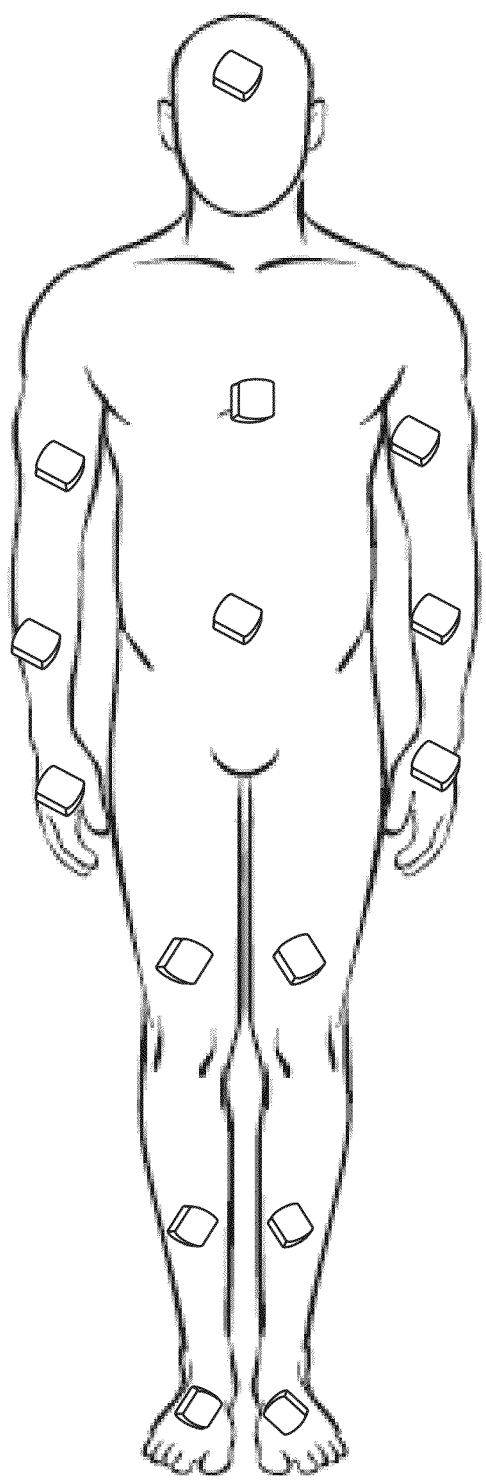
FIGS. 6a, 6b, and 6c illustrate the postures performed by a user for mapping calibration and calibration of body segment (limb) dimensions.

502. The user 101 locates their left and right foot in footprint L1 and footprint 1 of footprint template 300 separately (footprint pair (L1, 1)). This represents an initial predetermined position, which is the initial standing posture. This posture is illustrated in FIG. 6a. The user may keep stationary for approximately 5 to 10 seconds to register this posture into the computer 106. That is, the computer 106 receives and stores an initial set of orientation signals from sensors 102a-103h for the initial predetermined position.

Figure 6B:
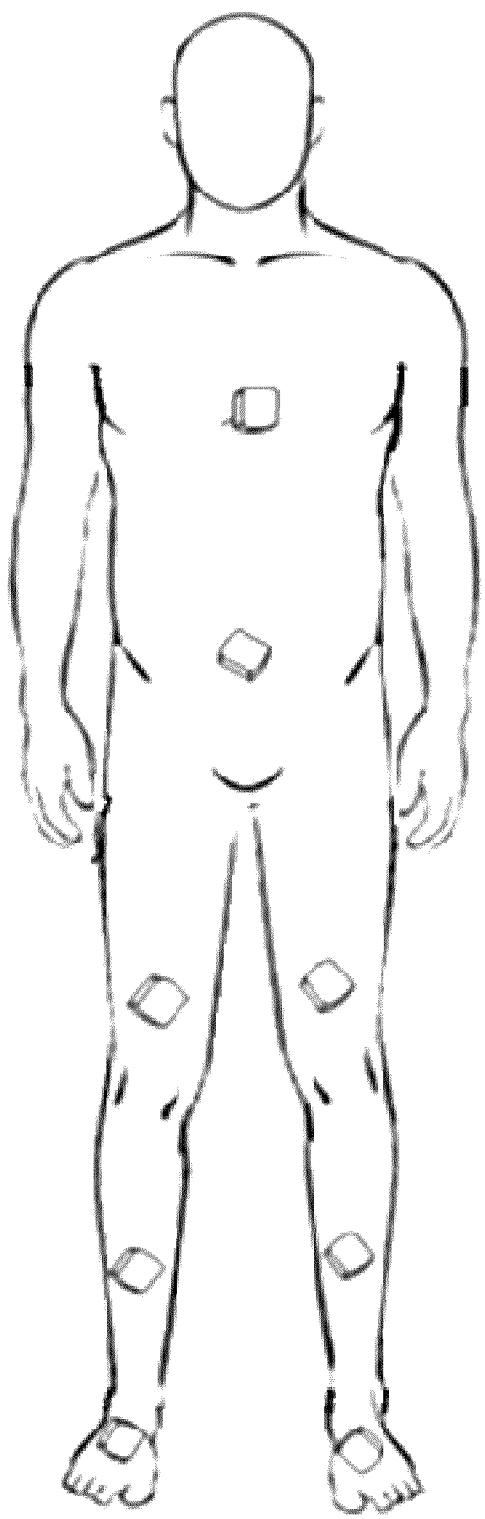

503. The user 101 keeps the left foot stationary in footprint L1 and unfolds their right foot to match it with footprint No. 2 (footprint pair (L1, 2)). The user stands naturally facing the front with their legs forming a "A" posture as shown in FIG. 6b. The user 101 keeps stationary for approximately 5 to 10 seconds to register this posture into the computer.

The user 101 keeps the left foot stationary in footprint L1 and unfolds their right foot to match it with footprint no. 3 (foot print pair (L1, 3)). The user 101 keeps stationary for approximately 5 to 10 seconds to register this posture into the computer.

For footprint template 300, there are a total of 18 location pairs for the left and the right foot. However, the user does not need to match with all of these footprints. From preliminary testing results, matching eight footprints already can provide good estimations. Technical details of using the orientation signals for calibrating/recalibrating the motion tracking system are provided below.

In FIG. 3, the numbers within brackets represent the case when the left foot is located at footprint (L2). Take note that the footprint No. 16 to No. 18 represents the same step vector as the footprint No. 1 to No. 3. Therefore, there is no need to repeat the matching procedure for this combination. Here only the footprints No. 1 to No. 3 need to be registered because they are used not only to determine the skeleton dimension but also as initial predetermined positions for determining the body bearing angle. The other footprints can be selected by the users based on their body sizes.

Figure 6C:
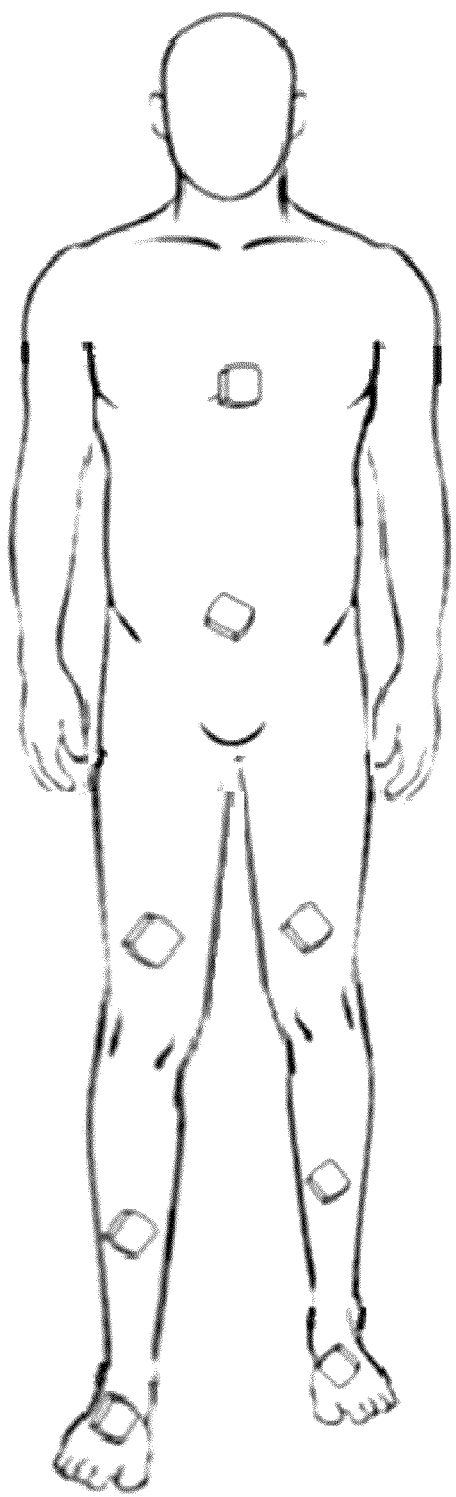

All the other selected footprints are matched and registered similarly, but these footprints can be matched using a more flexible posture because they are only used in skeleton model determination. For example, the user 101 may keep the left foot stationary on footprint L1 and unfold their right foot onto footprint 5. This posture is illustrated in FIG. 6c. In any event, the user 101 matches the pair of body segments representing their feet to a first set of predetermined positions (e.g. (L1, 1), (L1, 2), (L1, 3), (L1, 4), (L1, 5) . . . )), and the computer 106 receives the corresponding orientation signals from the sensors 102a-103h for each predetermined position.

The entire procedure can be completed within two or three minutes.

504. Based on the stored orientation signals and the known first set of predetermined positions, an efficient calibration algorithm can determine the skeleton dimension parameters and mapping automatically once the procedure is completed. Manual post processing of the data is not required.

Figure 5B:
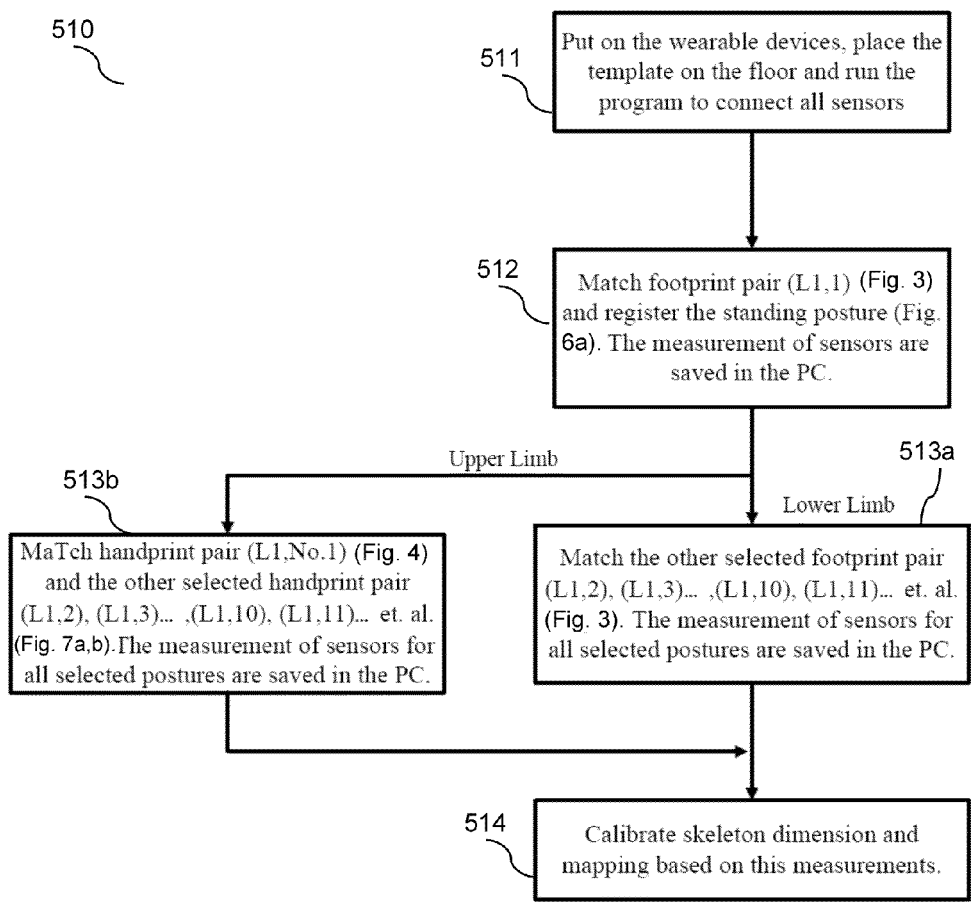
FIG. 5b illustrates a further example method according to the invention for calibrating dimensions for upper and lower body segments in a motion tracking system.

FIG. 5b is another flow diagram illustrating another example template based calibration procedure 510 for the lower body segments 104a-104g and upper body segments 105a-105h. The whole procedure may only require several footprint matching steps and several handprint matching steps to be completed over a short period of time such as, for example, within two to five minutes. It is to be appreciated that the following steps include actions performed by the user 101, which in no way limit the calibration procedure performed by computer 106. The steps of the calibration procedure 510 are as follows:

511. The user 101 wears the orientation sensors 102a-103h (e.g. IMUs), and runs the program to connect these sensors to the computer 106.

512. The user 101 locates his left and right foot in footprint L1 and footprint 1 using footprint template 300 separately, stands in the initial standing posture and keeps stationary for approximately 5 to 10 seconds to register this initial standing posture into the computer 106, this posture is shown in FIG. 6a.

Steps 513a and 513b may be performed at the same time, or one after the other in a serial fashion.

513a. Lower body segment calibration is performed in the same manner as in step 503 of procedure 500. Once step 513b has been performed, proceed to step 514.

513b. Upper body segment calibration is performed in a similar fashion as step 513a, where handprint template 400 is used as an example. Briefly, the user 101 keeps their left hand in stationary position L1 and unfolds his right hand to match it with handprint No. 1 on the handprint template 400. The user 101 keeps stationary for approximately 5 to 10 seconds to register this posture into the computer, the posture is shown for example in FIG. 8a. The user 101 keeps their left hand in stationary position L1 and unfolds his right hand to match it with handprint No. 2 on the handprint template 400. The user 101 keeps stationary for approximately 5 to 10 seconds to register this posture into the computer as shown in FIG. 8b. Similarly, the user 101 performs this registration procedure for other handprint pairs or predetermined positions (e.g. handprint pairs (L1, 1), (L1, 2), (L1, 3), (L1, 9) etc.) In any event, the user 101 matches the pair of body segments representing their hands to a second set of predetermined positions (e.g. (L1, 1), (L1, 2), (L1, 3), (L1, 4), (L1, 5) ... )), and the computer 106 receives the corresponding orientation signals from the sensors 102a-103h for each of the predetermined positions in the second set of predetermined positions.

514. Based on the stored orientation signals and the known first and second sets of predetermined positions, an efficient calibration algorithm can determine the skeleton dimension parameters and mapping automatically once the procedure is completed. Manual post processing of the data is not required.

The arm skeleton model or calibration of the upper body segments (limbs) was briefly described in step 513b. Some further details are now described in this respect. For calibration of the upper body segments 105a-105g (limbs), the procedure and calibration algorithm is similar to the calibration of the lower body segments 104a-104g as described in step 503 or 513a. As shown in FIG. 4, the handprint template 400 includes reference patterns that are used for the left and the right hands to locate at.

Figure 7A:
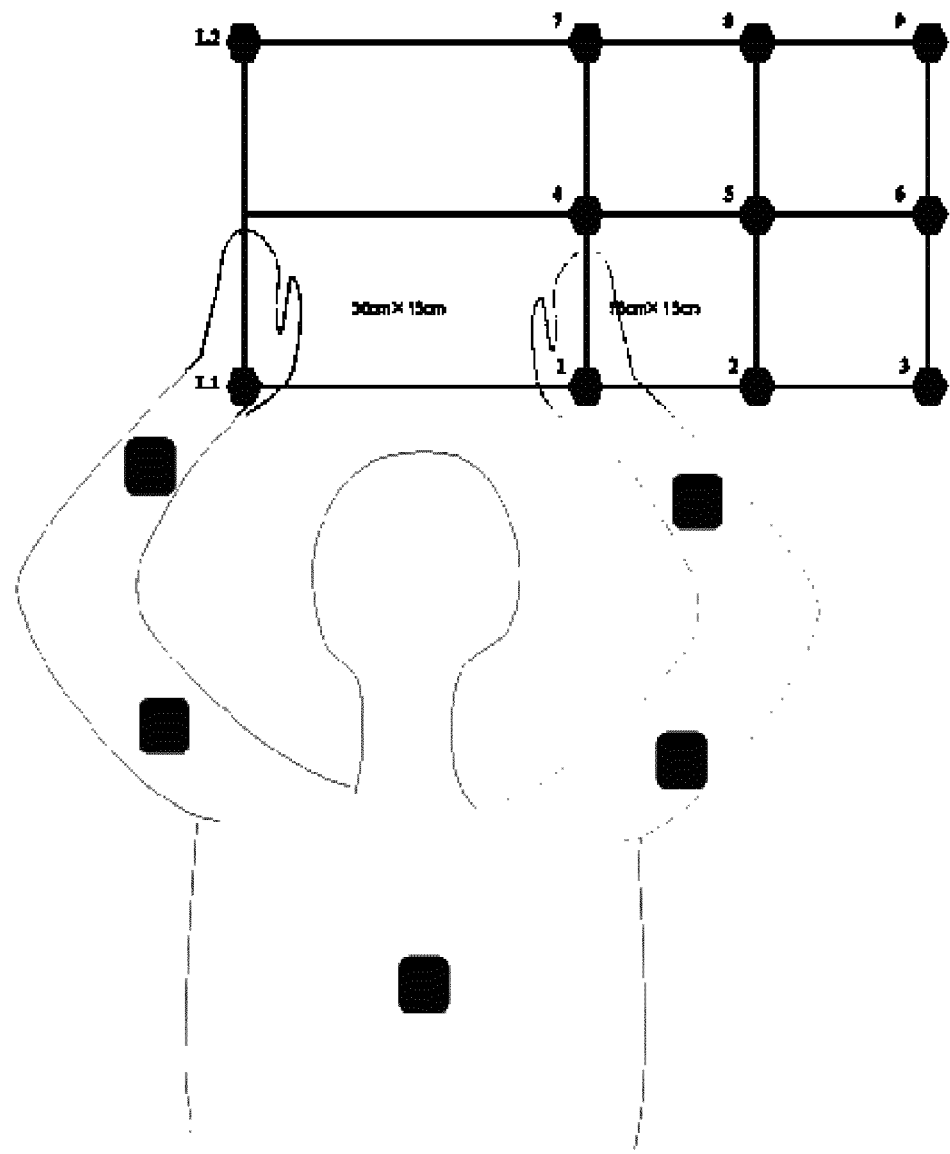
FIG. 7a illustrates an example method of calibration according to the invention for calibrating upper body segment (limb) dimensions using an example handprint template (the squares represent orientation sensors)

Mapping calibration for both upper body segments 105a-105g (limbs) and lower body segments 104a-104g may be completed at the same time. After the mapping calibration, the calibration procedures for the upper body segments 105a-105g are conducted as follows:

Firstly, the user 101 locates his left and right hand letting the middle of wrist joints 105a and 105f match the marker L1 and marker No. 1 separately (see for example FIG. 7(a)). The user 101 stands in the initial standing posture as in FIG. 1 or 6a and keeps stationary for 5 to 10 seconds to register this posture and the corresponding orientation signals into the computer 106.

Figure 7B:
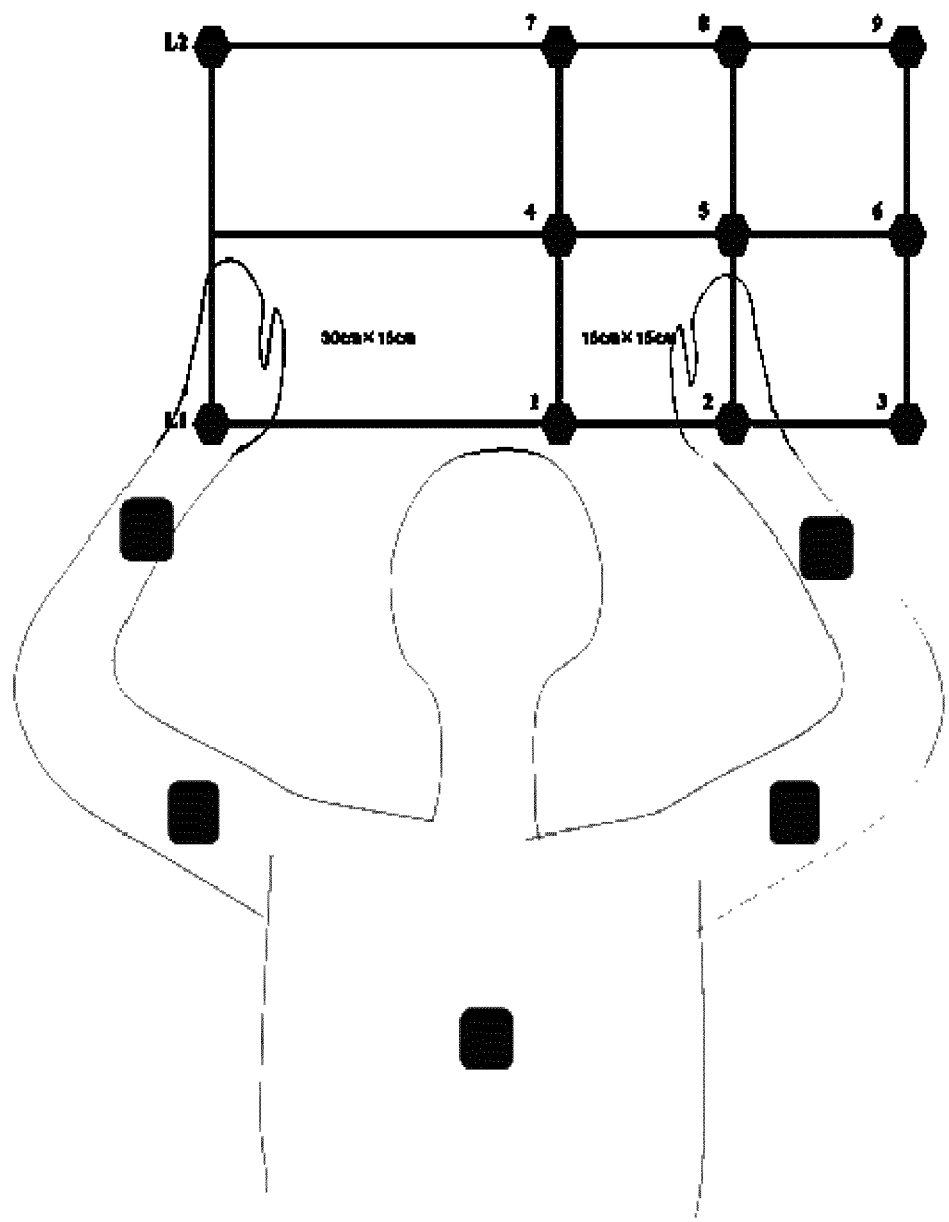
FIG. 7b illustrates another example method of calibration according to the invention for calibrating upper body segment dimensions (limb) using the example handprint template (the squares represent the orientation sensors)

Secondly, the user 101 keeps the left hand matching marker L1 and moves their right wrist (e.g. body segment 105f) to match it with marker No. 2 (see for example FIG. 7(b)). The user 101 stands in the corresponding standing posture (e.g. as shown in 6b) and keeps stationary for 5 to 10 seconds to register this posture and the corresponding orientation signals into the computer 106.

Thirdly, the user 101 performs the above procedure with left hand matching marker L1 and the right wrist matching the other hand markers in the same way as described in the second step.

As illustrated in FIG. 4, a total of 18 location pairs (predetermined positions) for the left and the right wrists are available in the handprint template 400. Once again, matching 8 hand marker pairs can optimize the upper limb skeleton model properly.

For different applications, the range of the main working space of the arm is different. Therefore, the weight or value to each marker may be assigned based on the importance of the point range in the application.

The technical details of the mapping calibration procedure will now be described with reference to FIG. 1. To present the spatial motion of all body segments 104a-105h, a set of coordinate systems are defined as illustrated in FIG. 1. First of all, the global coordinate frame $F_W$ is defined as the sensing reference coordinate frame. Since in all types of orientation sensors (or measurement devices), the coordinate can be defined according to developers, here $F_W$ is defined such that the X-axis points to the "north" (e.g. out of the page or FIG. 1), the Y-axis points to the "east" (e.g. towards the left of FIG. 1), and the Z-axis points "downward" (e.g. to the bottom of FIG. 1). The X, Y and Z axis points are orthogonal. This frame is defined as a global reference frame to describe the global 3D motions of the user (subject).

To represent the motion of the body, one body frame is defined for each of the body segments 104a-105h, as shown in FIG. 1. For convenience, the user 101 is illustrated in FIG. 1 as being in the initial standing posture; all the body coordinate systems of the user 101 are chosen such that the X-axis points forward, the Z-axis points downward. The Y-axis is determined such that a right-handed coordinate frame is formed. The origins of body segment coordinate frames (or body frames), as illustrated for each of the body segments 104a-105h, are chosen based on the skeleton model of the user 101. The body segment coordinate frames for body segments 104a-104g are labelled $F_{R3}$, $F_{R2}$, $F_{R1}$, $F_{L2}$, $F_{L3}$, and $F_0$, respectively.

As illustrated in FIG. 1, the body frames are in parallel during the initial standing posture. Therefore, in initial standing posture, there is only a rotation of the bearing angle along the Z-axis between all the body segment frames and the global frame $F_W$. Let $R_{iS}$ represent the directly measured orientation of the sensor i with respect to the global frame $F_W$, $R_{iM}$ represent the orientation of the sensor i in the corresponding $i^{th}$ body segment frame, and $R_i$ represent the orientation of the body segment frame in the global coordinate frame $F_W$. Then:

$$R_i R_{iM} = R_{iS} \quad (1)$$

When the body bearing angle ($\Phi$) of the initial standing posture is determined, the corresponding orientation of the body segment frames (e.g. $F_{R3}, F_{R2}, F_{R1}, F_{L1}, F_{L2}, F_{L3}$, and $F_0$ for the lower body segments 104a-104g) are determined as follows:

$$R_i = \mathrm{rotz}(\Phi), i = R2, R1, 0, L2, L1 \quad (2)$$

Since the sensor orientation is directly available from its outputs, the mappings can be calculated by:

$$R_{iM} = R_i^T R_{iS} \quad (3)$$

These mapping matrices are considered as constant after the sensors are properly mounted onto the body of the user 101 and until the user 101 performs a recalibration of the entire system 100.

Taking note that the body is symmetric through the longitudinal section in initial standing posture, the body dimension parameters are defined in Table I.

TABLE I

Skeleton dimension vectors

| Body Segment | Vector | From | To | Coordinate |
|---|---|---|---|---|
| Right Shank | $r_{R2}$ | Right Knee | Right Ankle | $(a, b, c)^T$ |
| Right Thigh | $r_{R1}$ | Right Hip | Right Knee | $(d, e, f)^T$ |
| Pelvis | $r_0$ | Left Hip | Right Hip | $(0, g, 0)^T$ |
| Left Shank | $r_{L2}$ | Left Knee | Left Ankle | $(d, -e, f)^T$ |
| Left Thigh | $r_{L1}$ | Left Hip | Left Knee | $(a, -b, c)^T$ |
| Right Upper Arm | $r_{R4}$ | Right | Right Elbow | $(a_U, b_U, c_U)^T$ |
| Right Forearm | $r_{R5}$ | Right Elbow | Right Wrist | $(d_U, e_U, f_U)^T$ |
| D_Shoulders | $r_1$ | Left Shoulder | Right | $(0, g_U, 0)^T$ |
| Left Upper Arm | $r_{L4}$ | Left Shoulder | Left Elbow | $(d_U, -e_U, f_U)^T$ |
| Left Forearm | $r_{L5}$ | Left Elbow | Left Wrist | $(a_U, -b_U, c_U)^T$ |

Here, since the kinematic hierarchy of the upper body segments (limbs) and the lower body segments (limbs) are the same, the following description is focussed on the lower body segments (limb) kinematics as an example. The upper body segment (limb) kinematics is the same form of calibration for the upper body segment (limb) dimensions.

The location of the foot is described by the location of ankle joint. Therefore, the vector from the left ankle joint 104a to the right ankle joint 104f is the stride or step vector $r_s$. For each specific footprint in template 300, the vector between the two feet is calculated based on the following equation:

$$r_s = R_{R2}r_{R2} + R_{R1}r_{R1} + R_0 r_0 - R_{L2}r_{L2} - R_{L1}r_{L1} \quad (4)$$

For the upper limb the vector between the wrists 105a and 105f are of the same form, thus is not repeated.

When a user 101 moves from the initial standing posture, for example in step 502 or 512 and illustrated in FIGS. 1 and 6a, to unfold foot posture as in steps 503 or 513a and illustrated in FIG. 6b, the translation of the pelvis along the X-direction is negligible. His legs mainly rotate along the X-direction. Based on this fact, the bearing of the user can be determined.

In initial standing posture (e.g. illustrated in FIGS. 1 and 6a), all body segment frames are in parallel and the orientations of all body frames are represented by $R_0$.

The step vector $r_s$ becomes:

$$r_s = R_0(r_{R2} + r_{R1} + r_0 - r_{L2} - r_{L1}) \quad (5)$$

When the user 101 unfolds his right foot sideward (e.g. as illustrated in FIG. 6a), the lower limb segments rotate along the X-direction for some angle $\theta_i$. As a result, for body segment i, its orientation becomes: $R'_i = R_0 \text{rotx}(\theta_i)$, substituting it into Equation (5), results in:

$$r'_s = \text{rotz}(\Phi)[\text{rotx}(\theta_{R2})r_{R2} + \text{rotx}(\theta_{R1})r_{R1} + \text{rotx}(\theta_0)r_0 - \text{rotx}(\theta_{L2})r_{L2} - \text{rotx}(\theta_{L1})r_{L1}] \quad (6)$$

Equation (6)-Equation (5), we have:

$$r'_s - r_s = \text{rotz}(\Phi) \sum_{i=R2}^{L2} (\text{rotx}(\theta_i) - I) r_i \quad (7)$$

Figure 8:
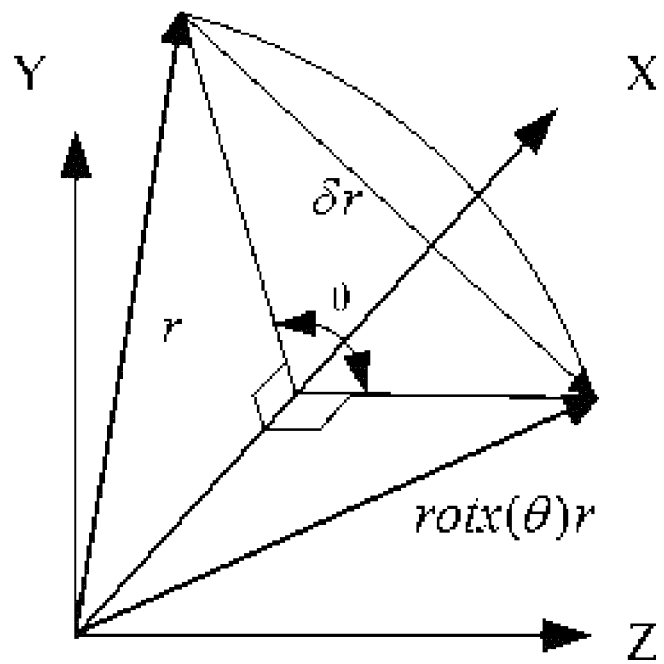
FIG. 8 illustrates a vector's rotation around the X-axis, based on which the bearing angle is determined.

Note that in FIG. 8, $\delta r = (\text{rotx}(\theta) - I)r$ is the difference between the vector r before and after rotation along the rotation axis (X-axis), see for example R. Murray, Z. Li, S. Sastry, and S. Sastry, A mathematical introduction to robotic manipulation: CRC, 1994; and J. McCarthy, Introduction to theoretical kinematics: MIT Press, Cambridge, Mass., 1990. Therefore, the difference $\delta r = (\text{rotx}(\theta) - I)r$ is always perpendicular to the X-axis as shown in FIG. 8. Thus, its coordinate can be written as $[0, y_i, z_i]^T$ $$r'_s - r_s = \text{rotz}(\Phi) \sum_{i=R2}^{L2} [0, y_i, z_i]^T = \text{rotz}(\Phi) \times [0, Y, Z]^T = \quad (8)$$
$$[-Y\sin(\Phi), Y\cos(\Phi), Z]^T = [x'_s - x_s, y'_s - y_s, z'_s - z_s]^T$$

Where $$Y = \sum_{i=R2}^{L2} y_i, Z = \sum_{i=R2}^{L2} z_i, \text{ and:}$$

$$\begin{cases} x'_s - x_s = -Y\sin(\Phi) \\ y'_s - y_s = Y\cos(\Phi) \end{cases} \quad (9)$$

From Equation (9), it is clear that when the foot is naturally unfolded facing a certain direction, the projection of the right foot location in the XOY plane is always along a line through the initial position $[x_s, y_s]^T$, and the tangent of this line is $-\cot(\Phi)$ regardless of whether the given skeleton is accurate or not. In other words, before calibrating the actual skeleton model, the bearing angle can be accurately calculated based on a virtual skeleton model, even though the dimension is not correct. Take note that this model is only for use of bearing angle estimation (not the one used in the final captured motion representation model), and its size doesn't matter because the detected bearing angle is the same regardless of what size of the model we use as shown in Equation (9). The skeleton model used for motion representation of the subject will be calibrated in the skeleton calibration procedure.

The bearing angle can be calculated as follow (when the right foot is unfolded, Y>0):

$$\Phi = \arctan 2(-(x'_s - x_s), y'_s - y_s) \quad (10)$$

Theoretically, two predetermined positions or points (e.g. footprints) are enough for the bearing estimation. In order to increase the reliability of the algorithm, from template 300 Nos. 1, 2, and 3 footprints are used to fit the line using the least square method, the bearing angle is determined subsequently. The mappings can be calibrated consequently as described in Equation (3).

After calibration of the constant mapping matrices, they can be used to update the actual movement or postures of the body by: $R_i = R_{iS} R_{iM}^T$ The technical details of the skeleton dimension parameter calibration (i.e. skeleton model determination) procedure will now be described with reference to FIG. 1. Body attached orientation sensors 102a-103h are able to track the orientations of body segments 104a-105h. If the skeleton dimension parameters are known, the stride or step vector $r_s$ from the left ankle 104a to the right ankle 104f can be calculated. The method starts from an inverse procedure to determine the skeleton dimensions with known footprint locations and captured orientation of the body segments 104a-105h. The skeleton dimension parameters are obtained through solving the kinematic chain equations.

In step vector calculation, substituting the parameters in Table I into Equation (4) results in the following equations for the lower body segment (limb) kinematics (e.g. body segments 104a-104g):

$$r_s = R_{R2}\begin{pmatrix}a\\b\\c\end{pmatrix} + R_{R1}\begin{pmatrix}d\\e\\f\end{pmatrix} + R_0\begin{pmatrix}0\\g\\0\end{pmatrix} - R_{L2}\begin{pmatrix}a\\-b\\c\end{pmatrix} - R_{L1}\begin{pmatrix}d\\-e\\f\end{pmatrix} \quad (11)$$

The equation system for the upper body segment (limb) kinematics (e.g. body segments 105a-105g) is of the same form as follows:

$$r_h = R_{R4}\begin{pmatrix}a_U\\b_U\\c_U\end{pmatrix} + R_{R5}\begin{pmatrix}d_U\\e_U\\f_U\end{pmatrix} + R_0\begin{pmatrix}0\\g_U\\0\end{pmatrix} - R_{L4}\begin{pmatrix}a_U\\-b_U\\c_U\end{pmatrix} - R_{L5}\begin{pmatrix}d_U\\-e_U\\f_U\end{pmatrix}$$

Since the calibration model of the upper body segments (limbs) and the lower body segments (limbs) are the same, the lower body segment calibration will be used as an example. The upper body segments can be calibrated in the same manner, where the dimension of the upper arm, forearm and the shoulder distances are the calibrating parameters. This is not repeated here.

Rearranging Equation (11), results in:

$$r_s = A_{ftp} \cdot [a,b,c,d,e,f,g]^T \quad (12)$$

where: $A_{ftp} = [R_{R2} + R_{L2} \cdot \text{diag}(-1,1,-1), R_{R1} + R_{L1} \cdot \text{diag}(-1,1,-1), R_0(:,2)]$ Here $R_X(:,i)$ means the i-th column of the matrix $R_X$, and $A_{ftp}$ is a 3×7 matrix which is a mapping between the body skeleton dimension parameters and the step vector from the left ankle body segment 104a to the right ankle body segment 104f. diag(−1,1,−1) is a 3×3 matrix diagonal matrix with −1,1,−1 being the diagonal elements.

Assuming the orientation signals from a total of n predetermined positions or footprints are registered, then using the orientation signals to calculate the stride or step vectors for all the n predetermined positions or footprints, combining all the step vectors and all the resulting $A_{ftp}$ matrices for each corresponding footprint (and concatenating all the matrixes), the following equation is obtained:

$$\begin{bmatrix}r_s^1\\r_s^2\\\ldots\\r_s^{n-1}\\r_s^n\end{bmatrix} = \begin{bmatrix}A_{ftp}^1\\A_{ftp}^2\\\ldots\\A_{ftp}^{n-1}\\A_{ftp}^n\end{bmatrix} \cdot [a,b,c,d,e,f,g]^T \quad (13)$$

Or in a compact way: AX=B, where B is a 3n×1 matrix, A is a 3n×7 matrix, $x=[a,b,c,d,e,f,g]^T$, and (n) is the number of footprints or predetermined positions for which orientation signals have been registered. In order to achieve the skeleton dimension for accurate estimation of step length for walking, fifteen footprints locations are available to cover the normal step area in the predetermined footprint set. Therefore, this system of linear equations is an over-constrained linear algebraic equation as the number of rows is much more than that of its columns.

Note from Equation (12) that $A_{ftp}^i$ is a transformation matrix that maps the skeleton parameter to the stride length vector. It maps the estimated solution X* to the estimated stride length vector by: $A_{ftp}^i X^* = r_s^{i*}$. Here i represent the ith footprint.

The desired solution of X* is to let all the estimated right foot position $r_s^{i*}$ as close as possible to the reference footprint locations. Thus, the following cost function needs to be minimized:

$$f(X^*) = \sum_{i=1}^{n}(r_s^{i*} - r_s^i)^T(r_s^{i*} - r_s^i) = \sum_{i=1}^{n} d_e^2 \quad (14)$$

Here $d_e$ represent the distance between the estimated stride vector and the reference vector known from the pre-designed vector between the footprints.

Fortunately, the left pseudo-inverse method provides the least square solution of the linear equations system (see A. Ben-Israel and T. Greville, Generalized inverses: Theory and applications: Springer Verlag, 2003):

$$X = (A^T \cdot A)^{-1} \cdot A^T \cdot B \quad (15)$$

This solution minimizes the following expression:

$$E = \sum_{i=1}^{n}(A_{ftp}^i X - r_s^i)^T(A_{ftp}^i X - r_s^i) = (AX - B)^T \cdot (AX - B) \quad (16)$$

Substituting $A_{ftp}^i X^* = r_s^{i*}$ into Equation (16), the following equation is obtained:

$$E = \sum_{i=1}^{n}(A_{ftp}^i X - r_s^i)^T(A_{ftp}^i X - r_s^i) = \sum_{i=1}^{n}(r_s^{i*} - r_s^i)^T(r_s^{i*} - r_s^i) = \sum_{i=1}^{n} d_e^2 \quad (17)$$

This is exactly the desired result for skeleton model estimation. Therefore, this optimized solution achieves the result that make the result best fit the calculated foot locations to the reference footprints or the first set of predetermined positions.

Note that for different applications, the weight or value of the footprints might be different for different applications or different types of sensors. For example, in normal walking applications, the accuracy in the step range is more important. Therefore, from footprint template 300 the sideward footprints like No. 3, 6, and 9 are less important, which leads to different weights in the skeleton estimation. Let $\xi_1$ denotes the weight of the footprint i in the estimation as described in the following cost function:

$$f(X^*) = \sum_{i=1}^{n}\xi_i\left[(r_s^{i*} - r_s^i)^T(r_s^{i*} - r_s^i)\right] = \sum_{i=1}^{n}\xi_i d_e^2 \quad (18)$$

Here, the only modification needed for the skeleton estimation equation is to multiple the square root of the weight to the corresponding Equation Error! Reference source not found. as follow:

$$\begin{bmatrix}\lambda_1 r_s^1\\\lambda_2 r_s^2\\\ldots\\\lambda_{n-1} r_s^{n-1}\\\lambda_n r_s^n\end{bmatrix} = \begin{bmatrix}\lambda_1 A_{ftp}^1\\\lambda_2 A_{ftp}^2\\\ldots\\\lambda_{n-1} A_{ftp}^{n-1}\\\lambda_n A_{ftp}^n\end{bmatrix} \cdot [a,b,c,d,e,f,g]^T; \quad (19)$$

-continued where: $(\lambda_i)^2 = \xi_i$.

Or in a compact way: $A_m X = B_m$. Then, the result to achieve the minimized cost function is provided by: $X = (A_m^T \cdot A_m)^{-1} \cdot A_m^T \cdot B_m$.

The kinematic chain equation for the upper body skeleton dimension for the second set of predetermined positions (or the handprints) is based on:

$$\begin{bmatrix} r_{sU}^1 \\ r_{sU}^2 \\ \ldots \\ r_{sU}^{n-1} \\ r_{sU}^n \end{bmatrix} = \begin{bmatrix} A_{ftpU}^1 \\ A_{ftpU}^2 \\ \ldots \\ A_{ftpU}^{n-1} \\ A_{ftpU}^n \end{bmatrix} \cdot [a_U, b_U, c_U, d_U, e_U, f_U, g_U]^T \quad (20)$$

where $r_{sU}^m$ is the span vector for the m-th predetermined position for $1 \leq m \leq n$ of the second set of predetermined positions (e.g. n handprint pairs), and $A_{ftpU}^m$ is the $A_{ftpU}$ matrix associated with the m-th predetermined position of the second set of predetermined positions, where $A_{ftpU}$ defines a mapping between the upper body skeleton dimension parameters $[a_U, b_U, c_U, d_U, e_U, f_U, g_U]$ and the associated span vector and is defined by: $A_{ftpU} = [R_{R4} + R_{L4} \cdot \text{diag}(-1,1,-1), R_{R5} + R_{L5} \cdot \text{diag}(-1,1,-1), R_1(:,2)]$, where $R_X(:,i)$ is the i-th column of the matrix $R_X$, $\text{diag}(-1,1,-1)$ is a diagonal matrix, $R_{R4}$, $R_{L4}$, $R_{R5}$, $R_{L5}$, and $R_1$ are the orientations of the corresponding body segments calculated from the corresponding orientation signals and the corresponding calibrated mapping. As an option, the method includes weighting each of the span vectors with an adjustable set of weights depending on the importance of each span vector. The kinematic chain equations for the upper body segments 105a-105g may be solved in the same manner as that for the lower body segments 104a-104g.

Since there are seven unknown parameters for both the lower body segment (limb) and the upper body segment (limb) dimension calibration, at least three points are needed to estimate the skeleton dimensions for lower limbs (and upper limbs), otherwise the rank of the A matrix will be less than seven which leads to infinity solution in the linear equations system. But for a reliable estimation of the skeleton model, the number of footprints (handprints) in use cannot be too small. Eight footprints (handprints) can work properly based on some preliminary experiments. Matching the templates is very easy and fast. Thus for the entire procedure, it only takes around five minutes before the skeleton model is determined.

The skeleton and mapping determination/calibration methods as described only depend on the measurement from the orientation sensors (tracking devices). It can be applied to calibrate all kinds of orientation based systems such as inertial, mechanical, magnetic and optical based systems.

Figure 9:
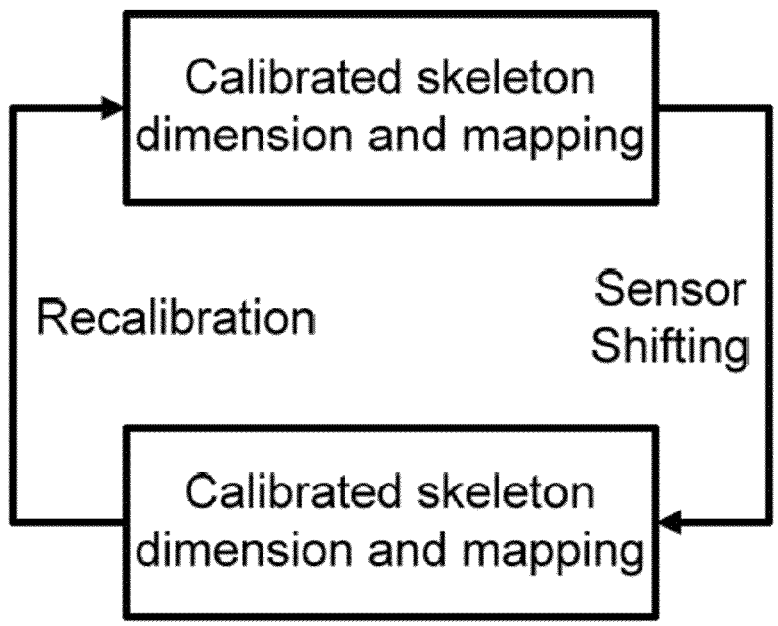
FIG. 9 illustrates an example method according to the invention for recalibrating the sensors of a motion tracking system due to sensor shift.

FIG. 9 illustrates an example method for recalibrating the motion tracking system. Once the dimensional parameters of the skeleton model are calibrated, the skeleton model of the subject is registered or stored in the system for future use. For long durations or dynamic motion tracking such as jogging and material arts, a slight shift of the sensors is inevitable, which can lead to large inaccuracy in the captured results.

Therefore, recalibration is needed to minimize the effect of the sensor shifting. In these situations, a convenient and time-saving mapping calibration procedure is required. The above-mentioned method for calculating the body bearing angle ($\Phi$) using an initial posture (e.g. FIGS. 6a and 6b) can be used to recalibrate the motion tracking system. This is a very convenient and fast method to use for real-time orientation based motion tracking (or capture) systems. After conducting the motion for a certain time, the system can be recalibrated easily to eliminate the sensor shifting problems.

During the set-up calibration (initialization) procedure, the skeleton model of the subject is already determined. Since the body segment (limb) dimensions of a subject do not change, only the mappings need to be recalibrated. This means that the recalibration procedure is simply the first half of the initialization procedure, i.e. the procedure that calculates the body bearing angle ($\Phi$) and then the mapping matrices $R_{iM} = R_i^T R_{iS}$ as described above with respect to equations (1) to (10). The user 101 only needs to register the initial standing posture, and then unfold his right foot sideward (e.g. from the posture in FIGS. 6a to 6b) to complete a recalibration procedure. If necessary, this may be performed without the footprint template. The recalibration method is a very flexible and reliable procedure for practical applications especially for exercises and sports training in both home environments and outdoor environments. Since no external devices and special constraints of the body are required, the methods as described herein can show advantage in motion tracking applications in both long duration and large unsupervised environments scenarios.

Referring to FIG. 1, the orientation of the trunk body segments 102g and 105g and the head body segment 105h are usually important in most of the motion tracking applications. Mapping calibration may be completed together with the upper and lower body segments 104a-105h (limbs). The dimensions of the trunk and head segments can be estimated from the height of the user 101. Except for the biomedical study of the trunk, where more detail anatomy skeleton model of the spine or the neck is needed, these head and trunk dimension estimations can be acceptable for most of the applications.

In this way, the calibration of the whole body skeleton dimension and the mappings are quickly calibrated within a short period of time (e.g. 5 minutes). The calculated skeleton model based on the methods according to the invention provides a good estimation of the 3D skeleton model.

Figure 10:
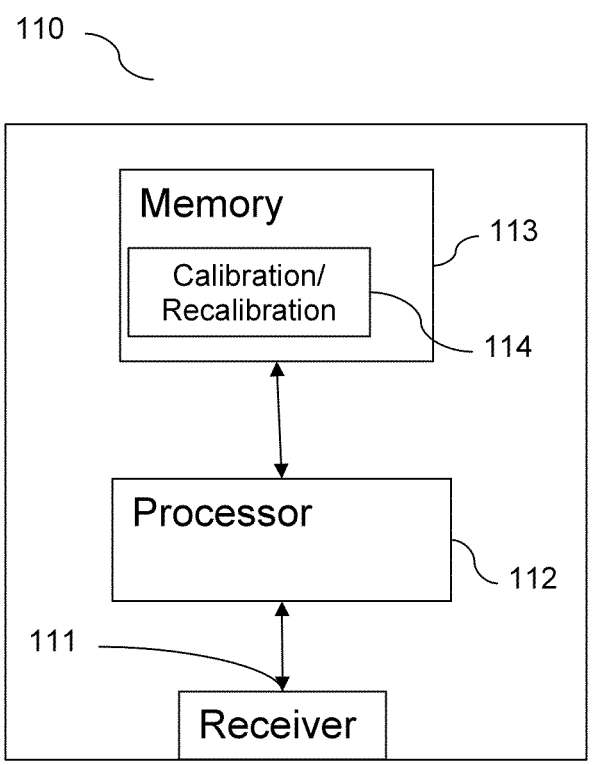
FIG. 10 illustrates an apparatus according to the invention.

FIG. 10 illustrates an apparatus 110 for use in calibrating a motion tracking system. The motion tracking system includes a plurality of sensors attached to a plurality of body segments of a user. The apparatus 110 includes a receiver 111, a processor 112 and a memory 113, the processor 112 being connected to the receiver 111 and the memory 113. The memory 113 may store files, sensor measurement data such as the orientation signals or corresponding data received from the plurality of sensors, and include various applications/programs/executable files that are implemented by the processor 112. The applications/programs/executable files stored in the memory 113, and implemented by the processor 112 may include calibration/recalibration procedures 114 according to the invention or as described above with reference to FIGS. 1 to 9.

In operation, the receiver 111 is adapted to receive a first set of orientation signals from a first set of the orientation sensors, the first set of orientation signals associated with a first pair of the body segments matching a first set of predetermined positions. The processor 112 is adapted to calibrate the skeleton dimension of the user and the mapping between the body segments and the corresponding attached sensors based on the first set of orientation signals.

The user may use a first template (e.g. a footprint template) including the first set of predetermined positions (e.g. footprints) and the first pair of the body segments include the left and right feet of the user. The receiver 111 is further adapted to receive an orientation signal from each of the first set of sensors as the left and right feet of the user are placed on each of the first set of predetermined positions of the template.

The receiver 111 may be further adapted to receive a second set of orientation signals from a second set of the sensors. The second set of orientation signals associated with a second pair of the body segments (e.g. hands) matching a second set of predetermined positions, where the second pair of body segments are different to the first pair of body segments. The processor 112 is further adapted to calibrate the skeleton dimensions of the user and the mapping between the motion of the body segments and the corresponding attached second set of sensors based on the second set of orientation signals.

The user may use a second template (e.g. a handprint template) that includes the second set of predetermined positions (e.g. handprints) and the second pair of the body segments includes the left and right hands of the user. The receiver 111 is further adapted to receive an orientation signal from each of the second set of sensors as the left and right hands of the user are placed on each of the second set of predetermined positions of the second template.

The mapping calibration may be performed by the apparatus 110, where the processor 112 is further adapted to calculate a user bearing angle, $\Phi$, based on the orientation signals from the first set of sensors when the first pair of body segments match an initial set of predetermined positions from the first set of predetermined positions. The processor 112 may be further adapted to calibrate the mapping for each of the plurality of orientation sensors between the body segment and the corresponding sensor based on the user bearing angle, $\Phi$.

As an example mapping calibration procedure performed by apparatus 110, the processor 112 may be further adapted to calibrate the mappings by calculating sensor orientation mapping matrices $R_{iM} = \text{rotz}(\Phi)^T R_{iS}$, for all of the sensors i, where $R_{iS}$ is an orientation matrix representing the measured orientation signal of sensor i with respect to a global coordinate frame at a particular measurement time, $R_{iM}$ is the sensor orientation mapping matrix of the sensor i in the corresponding body segment M, and $\text{rotz}(\Phi)$ is a rotation matrix representing a rotation of $\Phi$ radians about the z-axis and represents the estimated orientation of the body segment corresponding to the initial set of predetermined positions. The processor 112 may be further adapted to update the motion of the body segments by calculating $R_i = R_{iS} R_{iM}^T$, where $R_i$ is the orientation of the sensor i corresponding to the body segment M in the global coordinate frame.

The calibration procedure for determining or calibrating the skeleton dimensions of the user may be performed by the apparatus 110. The processor 112 may be further adapted to calibrate the skeletal dimensions of the user by calculating from the first set of predetermined positions a corresponding set of step vectors between the first pair of body segments, and calculating lower body skeleton dimension parameters by solving a kinematic chain equation based on the step vectors and the corresponding orientation signals.

In addition, the processor 112 may be further adapted to calibrate the skeletal dimensions of the user by calculating from the second set of predetermined positions a corresponding set of span vectors between the second pair of body segments, and calculating upper body skeleton dimension parameters by solving a kinematic chain equation based on the span vectors and the corresponding orientation signals.

The apparatus 110 may also perform recalibration of the motion tracking system, where the processor 112 is further adapted to recalibrate the motion tracking system by recalculating a new user bearing angle, $\Phi$, based on the orientation signals from the first set of sensors when the first pair of body segments match an initial set of predetermined positions from the first set of predetermined positions. Calibrating the mapping for each of the plurality of orientation sensors between the body segment and the corresponding sensor based on the user bearing angle, $\Phi$.

The recalibration procedure may be performed by a recalibration apparatus (not shown) for recalibrating the motion tracking system. The recalibration apparatus may include a receiver, a processor and a memory, the processor connected to the receiver and the memory.

The memory 113 may be adapted to store the received orientation signals, the calibrated skeleton dimensions and/or the mappings for use in calibrating, recalibrating, analysis and tracking the motion of the user. The orientation sensors may be any suitable spatial orientation sensor or marker. For example, the orientation sensors may be at least one of the sensors from the group of orientation tracking devices, magnetic trackers, inertial measurement units, marker groups, or other sensing devices that provide spatial orientation.

In operation, the receiver is adapted to receive a first set of orientation signals from a first set of the orientation sensors, the first set of orientation signals associated with a first pair of the body segments matching a set of predetermined positions. The processor is adapted to calculate a user bearing angle, t, based on the orientation signals from the first set of sensors, and calibrate the mapping for each of the plurality of orientation sensors between the body segment and the corresponding sensor based on the user bearing angle, $\Phi$. The memory may be adapted to store the mappings and/or the orientation signals for use in tracking the motion of the user.

The above examples of the invention have described various calibration methods and apparatus for initialization (initial calibration) and recalibration of spatial orientation tracker based motion capture systems. Further examples and modifications are described by way of example only. The templates as described may include well designed footprints in several pre-determined locations or positions as shown in FIG. 3 and well designed handprints in several pre-determined locations or positions as shown in FIG. 4. In the calibration methods, the 3-dimensional skeleton models for the spatial motion representation and the mapping between the body motion and the sensor motion are determined based on a quick pre-defined and organized footprint (handprint) matching procedure. Different sizes of footprints are available for users in different sizes. Both the mapping calibration and the skeleton determination can be completed simultaneously in the same template matching procedure.

The orientation sensors or tracking devices in the system can be any type of sensor (magnetic trackers, inertial measurement units IMUs, marker groups, or other sensing devices) so long as they provide the spatial orientation results.

The bearing angle of the subject is determined based on naturally unfolding the foot as shown in steps 502, 504, 512, 514 with respect to FIGS. 5a and 5b and in FIGS. 6a to 6b and described in the mapping calibration procedure. This is used to determine the mapping between sensor and body segment motions. No measurements of the body parameters or regression data are needed for skeleton determination. The skeleton model may be first modelled based on the symmetric properties of the human body with unknown parameters. These parameters can be determined through solving the kinematic chain equation from the left ankle to the right ankle (the left wrist to the right wrist). The kinematic chain equation can be an over constrained linear algebra system whose optimal solution can be estimated through the left pseudo-inverse. The skeleton model may be used with symmetric properties. A weighting may be applied to all footprints or predetermined positions (handprints) and can be adjusted based on their importance in the corresponding motion tracking/capture applications.

This recalibration procedure is based on natural movements from the initial standing posture to the posture of standing with feet unfold. This can be conducted anywhere at any time without any external assistive devices or known reference directions.

The above-mentioned methods, procedures, algorithms according to the invention as described herein may be implemented as a computer program, comprising computer readable code which, when executed on a processor, causes the processor to perform the steps of any of the methods, procedures, or algorithms as described. For example, a computer program, comprising computer readable code which, when executed on a processor, may cause the processor to perform the steps of the calibration mapping methods/procedures according to the invention. In another example, a computer program, comprising computer readable code which, when executed on a processor, may cause the processor to perform the steps of the skeleton dimension calibration methods/procedures according to the invention. There may be one or more computer program products comprising a computer readable medium and one or more computer programs as described, where the computer program(s) is stored on the computer readable medium. The compute programs may be executed on the computer 106 or apparatus 110.

Although the invention has been described in terms of embodiments or examples as set forth above, it should be understood that these embodiments or examples are illustrative only and that the claims are not limited to those embodiments or examples. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A method of calibrating a motion tracking system comprising a plurality of orientation sensors attachable to a plurality of body segments of a user, the plurality of orientation sensors being communicatively coupled to a computer, the method comprising the steps of:
receiving, at the computer, a first set of orientation signals from a first set of the orientation sensors, the first set of orientation signals associated with a first pair of the body segments matching a first set of predetermined positions, wherein the first pair of the body segments comprise corresponding body segments on different sides of the body of the user;
calibrating, by the computer, the skeleton dimension of the user and a mapping between the body segments and the corresponding attached sensors based on the first set of orientation signals, wherein calibrating the mapping comprises determining, by the computer for each sensor of the first set of the orientation sensors, a body segment of the plurality of body segments associated with the sensor,
wherein calibrating the skeletal dimensions of the user further comprises the steps of:

calculating, by the computer, from the first set of predetermined positions a corresponding set of step vectors between the first pair of body segments;
calculating, by the computer, lower body skeleton dimension parameters by solving a kinematic chain equation based on the step vectors and the corresponding orientation signals.

2. A method according to claim 1, wherein a first template comprises the first set of predetermined positions and the first pair of the body segments include the left and right feet of the user, wherein the step of receiving the first set of orientation signals includes receiving an orientation signal from each of the first set of sensors as the left and right feet of the user are placed on each of the first set of predetermined positions of the template.

3. A method according to claim 1, further comprising:
receiving a second set of orientation signals from a second set of the sensors, the second set of orientation signals associated with a second pair of the body segments matching a second set of predetermined positions, wherein the second pair of body segments are different to the first pair of body segments; and
wherein the step of calibrating further includes calibrating the skeleton dimension of the user and the mapping between the motion of the body segments and the corresponding attached second set of sensors based on the second set of orientation signals.

4. A method according to claim 3, wherein a second template comprises the second set of predetermined positions and the second pair of the body segments include the left and right hands of the user, wherein the step of receiving the second set of orientation signals includes receiving an orientation signal from each of the second set of sensors as the left and right hands of the user are placed on each of the second set of predetermined positions of the second template.

5. A method according to claim 1, wherein the calibrating step further comprises the steps of:
calculating a user bearing angle, $\Phi$, based on the orientation signals from the first set of sensors when the first pair of body segments match an initial set of predetermined positions from the first set of predetermined positions;
calibrating the mapping for each of the plurality of orientation sensors between the body segment and the corresponding sensor based on the user bearing angle, $\Phi$.

6. A method according to claim 5, wherein calibrating the mapping includes determining, for each of the sensors, the mapping between said each sensor and the corresponding body segment motions.

7. A method according to claim 5, wherein calculating the user bearing angle, $\Phi$, is based on a standard skeleton model with the symmetric properties of the human body.

8. A method according to claim 5, wherein the first pair of body segments correspond to at least the set of vectors defined in the table of:

| Body Segment | Vector | From | To | Coordinate |
| --- | --- | --- | --- | --- |
| Right Shank | $r_{R2}$ | Right Knee | Right Ankle | $(a, b, c)^T$ |
| Right Thigh | $r_{R1}$ | Right Hip | Right Knee | $(d, e, f)^T$ |
| Pelvis | $r_0$ | Left Hip | Right Hip | $(0, g, 0)^T$ |
| Left Shank | $r_{L2}$ | Left Knee | Left Ankle | $(d, -e, f)^T$ |
| Left Thigh | $r_{L1}$ | Left Hip | Left Knee | $(a, -b, c)^T$ | and;

wherein the kinematic chain equation for the lower body skeleton dimension for the first set of predetermined positions is based on:

$$\begin{bmatrix} r_s^1 \\ r_s^2 \\ \ldots \\ r_s^{n-1} \\ r_s^n \end{bmatrix} = \begin{bmatrix} A_{fp}^1 \\ A_{fp}^2 \\ \ldots \\ A_{fp}^{n-1} \\ A_{fp}^{n-1} \end{bmatrix} \cdot [a,b,c,d,e,f,g]^T,$$

where $r_s^m$ is the step vector for the m-th predetermined position for $1 \le m \le n$ of the first set of predetermined positions, and $A_{fp}^m$ is the $A_{fp}$ matrix associated with the m-th predetermined position, where $A_{fp}$ defines a mapping between the lower body skeleton dimension parameters [a, b, c, d, e, f, g] and the associated step vector and is defined by: $A_{fp} = [R_{R2}+R_{L2}\cdot\text{diag}(-1,1,-1), R_{R1}+R_{L1}\cdot\text{diag}(-1,1,-1), R_0(:, 2)]$, where $R_X(:,i)$ is the i-th column of the matrix $R_X$, diag(−1,1,−1) is a diagonal matrix, $R_{R2}, R_{L2}, R_{R1}, R_{L1}$, and $R_0$ are the orientations of the corresponding body segments calculated from the corresponding orientation signals and the corresponding calibrated mapping.

9. A method according to claim 8, further comprising weighting each of the step vectors with an adjustable set of weights depending on the importance of each step vector.

10. A method according to claim 1, wherein calibrating the skeletal dimensions of the user further comprises the steps of:
calculating from the second set of predetermined positions a corresponding set of span vectors between the second pair of body segments;
calculating upper body skeleton dimension parameters by solving a kinematic chain equation based on the span vectors and the corresponding orientation signals.

11. A method according to claim 10, wherein the second pair of body segments correspond to at least the set of vectors defined in the table of:

| Body Segment | Vector | From | To | Coordinate |
|---|---|---|---|---|
| Right Upper Arm | $r_{R4}$ | Right Shoulder | Right Elbow | $(a_U, b_U, c_U)^T$ |
| Right Forearm | $r_{R5}$ | Right Elbow | Right Wrist | $(d_U, e_U, f_U)^T$ |
| D_Shoulders | $r_1$ | Left Shoulder | Right Shoulder | $(0, g_U, 0)^T$ |
| Left Upper Arm | $r_{L4}$ | Left Shoulder | Left Elbow | $(d_U, -e_U, f_U)^T$ |
| Left Forearm | $r_{L5}$ | Left Elbow | Left Wrist | $(a_U, -b_U, c_U)^T$ | and;

wherein the kinematic chain equation for the upper body skeleton dimension for the second set of predetermined positions is based on:

$$\begin{bmatrix} r_{sU}^1 \\ r_{sU}^2 \\ \ldots \\ r_{sU}^{n-1} \\ r_{sU}^n \end{bmatrix} = \begin{bmatrix} A_{fpU}^1 \\ A_{fpU}^2 \\ \ldots \\ A_{fpU}^{n-1} \\ A_{fpU}^n \end{bmatrix} \cdot [a_U, b_U, c_U, d_U, e_U, f_U, g_U]^T,$$

where $r_{sU}^m$ is the span vector for the m-th predetermined position for $1 \le m \le n$ of the second set of predetermined positions, and $A_{fpU}^m$ is the $A_{fpU}$ matrix associated with the m-th predetermined position of the second set of predetermined positions, where $A_{fpU}$ defines a mapping between the upper body skeleton dimension parameters $[a_U, b_U, c_U, d_U, e_U, f_U, g_U]$ and the associated span vector and is defined by:

$A_{fpU} = [R_{R4}+R_{L4}\cdot\text{diag}(-1,1,-1), R_{R5}+R_{L5}\cdot\text{diag}(-1,1,-1), R_1(:,2)]$, where $R_X(:,i)$ is the i-th column of the matrix $R_X$, diag(−1,1,−1) is a diagonal matrix, $R_{R4}, R_{L4}, R_{R5}, R_{L5}$, and $R_1$ are the orientations of the corresponding body segments calculated from the corresponding orientation signals and the corresponding calibrated mapping.

12. A method according to claim 10, further comprising weighting each of the span vectors with an adjustable set of weights depending on the importance of each span vector.

13. A method according to claim 1, further comprising a step of recalibrating the motion tracking system by:
recalculating a user bearing angle, Φ, based on the orientation signals from the first set of sensors when the first pair of body segments match an initial set of predetermined positions from the first set of predetermined positions;
calibrating the mapping for each of the plurality of orientation sensors between the body segment and the corresponding sensor based on the user bearing angle, Φ.

14. An apparatus for calibrating a motion tracking system comprising a plurality of sensors attachable to a plurality of body segments of a user, the apparatus comprising a receiver, a processor and a memory, the processor being connected to the receiver and the memory; wherein:
the receiver is adapted to receive a first set of orientation signals from a first set of the orientation sensors, the first set of orientation signals associated with a first pair of the body segments matching a first set of predetermined positions;
the processor is adapted to calibrate the skeleton dimension of the user and a mapping between the body segments and the corresponding attached sensors based on the first set of orientation signals, wherein calibrating the mapping comprises determining, by the computer for each sensor of the first set of the orientation sensors, a body segment of the plurality of body segments associated with the sensor,
wherein the processor is further adapted to calibrate the skeletal dimensions of the user by:
calculating from the first set of predetermined positions a corresponding set of step vectors between the first pair of body segments;
calculating lower body skeleton dimension parameters by solving a kinematic chain equation based on the step vectors and the corresponding orientation signals.

15. An apparatus according to claim 14, wherein a first template comprises the first set of predetermined positions and the first pair of the body segments include the left and right feet of the user, wherein:
the receiver is further adapted to receive an orientation signal from each of the first set of sensors as the left and right feet of the user are placed on each of the first set of predetermined positions of the template.

16. An apparatus according to claim 14, wherein:
the receiver is further adapted to receive a second set of orientation signals from a second set of the sensors, the second set of orientation signals associated with a second pair of the body segments matching a second set of predetermined positions, wherein the second pair of body segments are different to the first pair of body segments; and the processor is further adapted to calibrate the skeleton dimensions of the user and the mapping between the motion of the body segments and the corresponding attached second set of sensors based on the second set of orientation signals.

17. An apparatus according to claim 16, wherein a second template comprises the second set of predetermined positions and the second pair of the body segments include the left and right hands of the user, wherein:

the receiver is further adapted to receive an orientation signal from each of the second set of sensors as the left and right hands of the user are placed on each of the second set of predetermined positions of the second template.

18. An apparatus according to claim 14, wherein:

the processor is further adapted to:

calculate a user bearing angle, $\Phi$, based on the orientation signals from the first set of sensors when the first pair of body segments match an initial set of predetermined positions from the first set of predetermined positions; and calibrate the mapping for each of the plurality of orientation sensors between the body segment and the corresponding sensor based on the user bearing angle, $\Phi$.

19. An apparatus according to claim 14, wherein the processor is further adapted to calibrate the skeletal dimensions of the user by:

calculating from the second set of predetermined positions a corresponding set of span vectors between the second pair of body segments;

calculating upper body skeleton dimension parameters by solving a kinematic chain equation based on the span vectors and the corresponding orientation signals.

20. An apparatus according to claim 14, wherein the processor is further adapted to recalibrate the motion tracking system by:

recalculating a user bearing angle, $\Phi$, based on the orientation signals from the first set of sensors when the first pair of body segments match an initial set of predetermined positions from the first set of predetermined positions; and calibrating the mapping for each of the plurality of orientation sensors between the body segment and the corresponding sensor based on the user bearing angle, $\Phi$.

21. A computer program stored on tangible computer readable medium, said program comprising computer readable code which, when executed on a processor, causes the processor to perform the steps of claim 1.

22. A computer program product comprising a tangible computer readable medium and a computer program according claim 21, wherein the computer program is stored on the tangible computer readable medium.

* * * * *